US011450805B2

(12) United States Patent
Nakasugi et al.

(10) Patent No.: US 11,450,805 B2
(45) Date of Patent: Sep. 20, 2022

(54) COMPOUND, SEMICONDUCTOR MATERIAL, AND METHODS FOR MANUFACTURING COATING AND SEMICONDUCTOR USING THE SAME

(71) Applicant: Merck Patent GmbH, Darmstadt (DE)

(72) Inventors: Shigemasa Nakasugi, Abiko (JP); Hiroshi Yanagita, Kakegawa (JP); Kazunori Kurosawa, Hamamatsu (JP); Takashi Sekito, Kakegawa (JP); Yusuke Hama, Kakegawa (JP); Yuriko Matsuura, Kakegawa (JP)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 16/471,136

(22) PCT Filed: Dec. 20, 2017

(86) PCT No.: PCT/EP2017/083685
§ 371 (c)(1),
(2) Date: Jun. 19, 2019

(87) PCT Pub. No.: WO2018/115043
PCT Pub. Date: Jun. 28, 2018

(65) Prior Publication Data

US 2020/0044158 A1 Feb. 6, 2020

(30) Foreign Application Priority Data

Dec. 21, 2016 (JP) ............................ JP2016-248434

(51) Int. Cl.
*H01L 51/00* (2006.01)
*C07C 39/04* (2006.01)

(52) U.S. Cl.
CPC .......... *H01L 51/0057* (2013.01); *C07C 39/04* (2013.01)

(58) Field of Classification Search
CPC ................................ H01L 51/00; C07C 39/04
See application file for complete search history.

(56) References Cited

U.S. PATENT DOCUMENTS 5,248,854 A * 9/1993 Kudoh .............. H01L 21/76885 174/261
5,518,824 A 5/1996 Funhoff et al.
5,972,247 A * 10/1999 Shi ........................ C09K 11/06 252/301.16
6,034,416 A * 3/2000 Uehara ............. H01L 27/11526 257/296
9,146,468 B2 9/2015 Hatakeyama et al.
2008/0299472 A1 12/2008 DeJong et al.
2009/0081582 A1* 3/2009 Hattori .................. G03F 7/0397 430/270.1
2010/0291475 A1* 11/2010 Li ........................ C09D 183/04 430/5
2011/0108811 A1 5/2011 Seo et al.
2011/0311915 A1* 12/2011 Kimura ................ G03F 7/0392 430/271.1
2015/0315333 A1 11/2015 Han et al.
2016/0111287 A1 4/2016 Hatakeyama et al.
2018/0039178 A1 2/2018 Suzuki et al.

FOREIGN PATENT DOCUMENTS

| | | | |
|---|---|---|---|
| EP | 0637899 | A1 | 2/1995 |
| EP | 0952200 | A2 | 10/1999 |
| JP | 11-312588 | A | 11/1999 |
| JP | 2009-080203 | A | 4/2009 |
| JP | 5653880 | B2 | 5/2013 |
| JP | 5200523 | B2 | 6/2013 |
| JP | 2015125843 | A | 7/2015 |
| JP | 2015-212378 | A | 11/2015 |
| JP | 2016081041 | A | 5/2016 |
| WO | WO-03007658 | A2 | 1/2003 |

OTHER PUBLICATIONS

International Search Report for PCT/EP2017/083685 dated Mar. 13, 2018.
Lim, Z., et al., "Synthesis and assessment of new cyclopenta-2,4-dienone derivatives for energy storage applications", Synthetic Metals, vol. 200, (2015), pp. 85-90.
Müller, M., et al., "Polycyclic Aromatic Hydrocarbons by Cyclodehydrogenation and Skeletal Rearrangement of Oligophenylenes", Angewandte Chemie International Edition English, vol. 36, No. 15, (1997), pp. 1607-1610.

(Continued)

*Primary Examiner* — Bijan Ahvazi
(74) *Attorney, Agent, or Firm* — Faegre Drinker Biddle & Reath LLP

(57) ABSTRACT

An object is to provide a semiconductor material and coating having high solubility in solvents and having advantageous filling property, high heat resistance, and/or high etching resistance. Another object is to provide a method for manufacturing a semiconductor using the semiconductor material. Still another object is to provide a novel compound. Provided are: a semiconductor material consisting of a specific aromatic hydrocarbon ring derivative; methods for manufacturing a coating and a semiconductor using the semiconductor material; and a compound consisting of a specific aromatic hydrocarbon ring derivative.

14 Claims, No Drawings

(56) References Cited

OTHER PUBLICATIONS

Written Opinion of the International Searching Authority for PCT/EP2017/083685 dated Mar. 13, 2018.
Harvey, J., et al., "Synthesis and Electronic Spectra of Substituted Bis(hexaphenylbenzenes)", Journal of Chemical and Engineering Data, vol. 22, No. 1, (1977), pp. 110-113.
Mikroyannidis, John A., "Wholly aromatic polyamides and polyimides prepared from 3,3?-di(4-aminophenyl)-5,5?-di(4-biphenylyl)-p-terphenyl and 3,3?-di(4-aminophenyl)-5,5?,6,6?-tetraphenyl-p-terphenyl", Polymer, vol. 40, 1999, pp. 3107-3117.
International Preliminary Report on Patentability received for PCT Patent Application No. PCT/EP2017/083685, dated Jul. 4, 2019, 8 pages.

* cited by examiner

COMPOUND, SEMICONDUCTOR MATERIAL, AND METHODS FOR MANUFACTURING COATING AND SEMICONDUCTOR USING THE SAME

CROSS-REFERENCE TO RELATED APPLICATIONS

This application is a national stage application (under 35 U.S.C. § 371) of PCT/EP2017/083685, filed Dec. 20, 2017, which claims benefit of Japanese Application No. 2016-248434, filed Dec. 21, 2016, both of which are incorporated herein by reference in their entirety.

TECHNICAL FIELD

The present invention relates to a novel compound and a semiconductor material. The present invention also relates to a method for manufacturing a semiconductor by a lithography technique, the method comprising forming a coating using the semiconductor material.

BACKGROUND ART

There are known a method for synthesizing a compound composed of monocyclic aromatic hydrocarbons linked to each other (Non Patent Literature 1) and graphenization accomplished by linking phenyls of such compounds to each other (Non Patent Literature 2). An attempt to use a graphene compound in a lithium-ion secondary battery has also been made (Patent Literature 1).

Production processes of semiconductors generally employ fine processing performed by lithography technology using a photoresist. The fine processing includes the steps of: forming a thin photoresist layer on a semiconductor substrate such as a silicon wafer; covering the layer with a mask pattern corresponding to the pattern of the intended device; exposing the layer with active light such as ultraviolet light through the mask pattern; developing the exposed layer to obtain a photoresist pattern; and etching the substrate using the obtained photoresist pattern as a protective coating, thus forming a fine unevenness corresponding to the above-described pattern. These photolithography steps suffer from reduction in the dimensional accuracy of the photoresist pattern due to the influence of standing waves resulting from reflection of light from the substrate or the influence of diffuse reflection of the exposure light by irregularities of the substrate. To solve this problem, methods of providing a bottom anti-reflective coating have been widely studied. The properties required of such a bottom anti-reflective coating include high anti-reflection performance.

Under these circumstances, an attempt to provide a resist underlayer comprising a polymer having a specific fluorene unit has also been made to achieve a reduction in reflectance and thereby allow a pattern with high dimensional accuracy to be formed by dry etching (Patent Literature 2). It has also been attempted to provide a resist underlayer that is capable of achieving a reduction in reflectance and that does not become wrinkled during etching on a substrate (Patent Literature 3).

CITATION LIST

Patent Literature

[Patent Literature 1] Japanese Patent No. 5200523 B

[Patent Literature 2] Japanese Patent Publication No. 2016-81041 A

[Patent Literature 3] Japanese Patent No. 5653880 B

[Non Patent Literature 1] Journal of Chemical and Engineering Data, James A. Harvey and Michael A. Ogliaruso. Vol. 22, No. 1, p 110-(1977)

[Non Patent Literature 2] Angew. Chem. Int. Ed. Engl. Markus Muller et al. 36 (No. 15), p 1607-(1997)

SUMMARY OF INVENTION

Technical Problem

The present inventors have got a concept that that a base material to be coated in a lithography process may be a non-flat substrate such as a stepped substrate and therefore that a composition capable of exhibiting advantageous coating formation property even when formed into a coating on a non-flat substrate is preferred. The present inventors have thought that it is desirable for the composition to be capable of being spread over the surface of a substrate or the like to be coated, and have therefore thought that it is important for the solid component of the composition to have high solubility in solvents. Additionally, the present inventors have conducted their study with emphasis on the heat resistance of the resulting coating, given that heat may be transferred to other neighboring layers during an etching process such as CVD.

As a result, the present inventors have successfully obtained a compound composed of specific monocyclic hydrocarbons linked to each other. Such a compound has high solubility in solvents and, when a composition comprising the compound is formed into a coating, the composition exhibits high performance in filling (gap filling) of fine processed structures including gaps. Additionally, a coating formed from such a composition has high heat resistance. The present inventors have further discovered that such a compound is suitable for forming an underlayer since it has high etching resistance and is capable of good gap-filling of a stepped substrate.

Solution to Problem

A semiconductor material according to the present invention consists of a compound represented by formula (I). The semiconductor material may also be referred to herein as a "semiconductor material represented by formula (I)".

$$X—Y \tag{1}$$

wherein:

X is a group represented by formula (2):

(2)

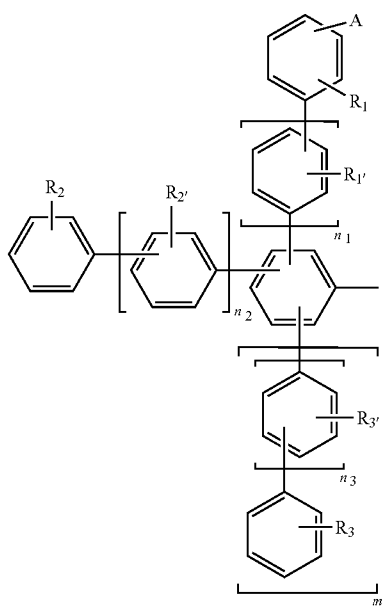

wherein

A is —OH, —$NH_2$, or —SH, $R_1$ is hydrogen, —OH, —$NH_2$, —SH, linear $C_{1-10}$ alkyl, branched $C_{3-10}$ alkyl, or a direct bond to a phenyl ring, $R_{1'}$ is hydrogen, —OH, —$NH_2$, —SH, linear $C_{1-10}$ alkyl, branched $C_{3-10}$ alkyl, or a direct bond to a phenyl ring, $R_2$ is hydrogen, —OH, —$NH_2$, —SH, linear $C_{1-10}$ alkyl, branched $C_{3-10}$ alkyl, or a direct bond to a phenyl ring, $R_{2'}$ is hydrogen, —OH, —$NH_2$, —SH, linear $C_{1-10}$ alkyl, branched $C_{3-10}$ alkyl, or a direct bond to a phenyl ring, $R_3$ is hydrogen, —OH, —$NH_2$, —SH, linear $C_{1-10}$ alkyl, branched $C_{3-10}$ alkyl, or a direct bond to a phenyl ring, $R_{3'}$ is hydrogen, —OH, —$NH_2$, —SH, linear $C_{1-10}$ alkyl, branched $C_{3-10}$ alkyl, or a direct bond to a phenyl ring, $n_1$ is 0, 1, or 2, $n_2$ is 0, 1, or 2, $n_3$ is 0, 1, or 2, m is 0, 1, 2, or 3, and;

Y is an aromatic hydrocarbon ring unsubstituted or substituted by one or more substituents selected from —OH, —$NH_2$, —SH, linear $C_{1-10}$ alkyl, or branched $C_{3-10}$ alkyl.

A composition according to the present invention comprises a semiconductor material according to the present invention and a solvent. An underlayer-forming composition according to the present invention comprises a composition according to the present invention.

A method for manufacturing a coating according to the present invention comprises applying a layer of a composition according to the present invention above a substrate and curing the layer. The phrase "above a substrate" as used herein to describe the manufacturing method means "at a location above a substrate". The term "above" means "upwardly of", and is intended to include the case where the layer of the composition is applied over and in contact with the substrate and the case where the layer of the composition is applied over the substrate with another layer interposed therebetween. When the coating to be manufactured by the manufacturing method is an underlayer, the phrase "above a substrate" means "at a location above a substrate and below a photoresist layer" or, in other words, means "at a location between a substrate and a photoresist layer". The term "below" means "downwardly of", and is intended to include the case where the layer of the composition is provided below and in contact with the photoresist layer and the case where the layer of the composition is provided below the photoresist layer with another layer interposed therebetween.

For example, a substrate-modifying layer may be formed over and in contact with a substrate, and an underlayer may be formed over and in contact with the substrate-modifying layer. And, a bottom anti-reflective coating may be formed over and in contact with an underlayer (a planarizing coating, for example) according to the present invention, and a photoresist layer may be formed over and in contact with the bottom anti-reflective coating.

A method for manufacturing a semiconductor according to the present invention comprises:

forming an underlayer according to the present invention;

forming a layer of a photoresist composition above the underlayer;

curing the photoresist composition to form a photoresist layer;

exposing the substrate coated with the photoresist layer;

developing the exposed substrate to form a resist pattern;

etching with the resist pattern as a mask; and processing the substrate.

Whether another etching step is performed between the above etching and the processing of the substrate can be selected depending on the process conditions. For example, an interlayer may be etched by the etching with the resist pattern as a mask, and then the substrate may be etched with the resulting interlayer pattern as a mask. Alternatively, an interlayer may be etched with the resist pattern as a mask, then an underlayer may be etched with the resulting interlayer pattern as a mask, and then the substrate may be etched with the resulting underlayer pattern as a mask. Alternatively, the substrate may be etched with the resist pattern as a mask only.

The present invention also provides a compound represented by formula (9)':

[Formula xii]

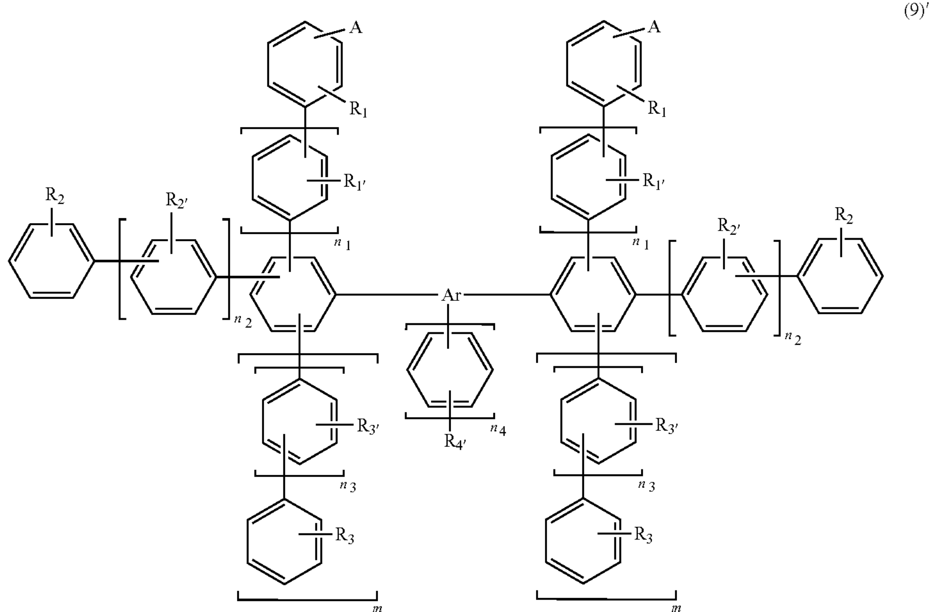

wherein

A is —OH, —$NH_2$, or —SH, $R_1$ is hydrogen, —OH, —$NH_2$, —SH, linear $C_{1-10}$ alkyl, branched $C_{3-10}$ alkyl, or a direct bond to a phenyl ring, $R_{1'}$ is hydrogen, —OH, —$NH_2$, —SH, linear $C_{1-10}$ alkyl, branched $C_{3-10}$ alkyl, or a direct bond to a phenyl ring, $R_2$ is hydrogen, —OH, —$NH_2$, —SH, linear $C_{1-10}$ alkyl, branched $C_{3-10}$ alkyl, or a direct bond to a phenyl ring, $R_{2'}$ is hydrogen, —OH, —$NH_2$, —SH, linear $C_{1-10}$ alkyl, branched $C_{3-10}$ alkyl, or a direct bond to a phenyl ring, $R_3$ is hydrogen, —OH, —$NH_2$, —SH, linear $C_{1-10}$ alkyl, branched $C_{3-10}$ alkyl, or a direct bond to a phenyl ring, $R_{3'}$ is hydrogen, —OH, —$NH_2$, —SH, linear $C_{1-10}$ alkyl, branched $C_{3-10}$ alkyl, or a direct bond to a phenyl ring, $n_1$ is 0, 1, or 2, $n_2$ is 0, 1, or 2, $n_3$ is 0, 1, or 2, m is 0, 1, 2, or 3, Ar is a $C_{6-20}$ aromatic hydrocarbon ring unsubstituted or substituted by a substituent selected from —OH, —$NH_2$, —SH, linear $C_{1-10}$ alkyl, or branched $C_{3-10}$ alkyl, $R_{4'}$ is hydrogen, —OH, —$NH_2$, —SH, linear $C_{1-10}$ alkyl, branched $C_{3-10}$ alkyl, or a direct bond to a phenyl ring, and $n_4$ is 0, 1, 2, 3, or 4, provided that the following compounds are excluded:

[Formula xiii]

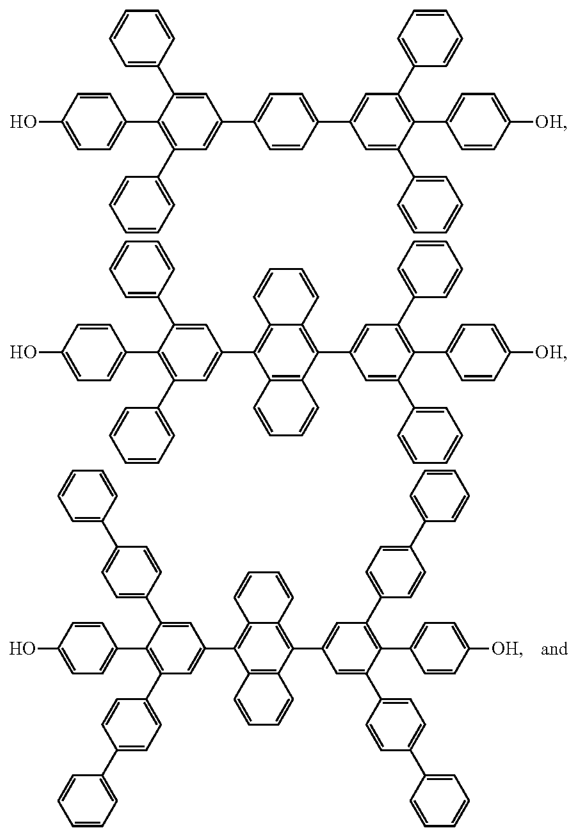

-continued

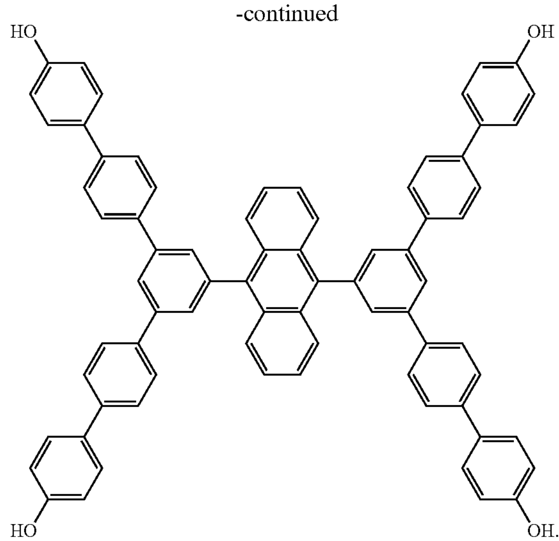

Effects of the Invention

The compound according to the present invention has high solubility in solvents, and a coating formed from a composition comprising the compound can exhibit improved coating formation property and is capable of gap-filling of a processed substrate. It has also been confirmed that the coating has high heat resistance, and shows less decrease in thickness after being heated.

DESCRIPTION OF EMBODIMENTS

The above summary and the following details are provided for illustration of the present invention, and are not intended to limit the claimed invention.

When a numerical range is specified herein using "-", the numerical range includes both of the numbers indicated before and after "-" and the unit is the same for the two numbers, unless otherwise explicitly stated. For example, "5-25 mol %" means "5 mol % or more and 25 mol % or less".

The terms such as "$C_{x-y}$", "$C_x$-$C_y$", and "$C_x$" as used herein represent the number of carbon atoms in a molecule or substituent. For example, "$C_{1-6}$ alkyl" refers to an alkyl chain having 1-6 carbon atoms (such as methyl, ethyl, propyl, butyl, pentyl, and hexyl).

When a polymer as described herein has plural types of repeating units, these repeating units are copolymerized. The copolymerization may be any one selected from alternating copolymerization, random copolymerization, block copolymerization, graft copolymerization, and any combination of any of these, unless otherwise explicitly stated.

The unit of temperatures as indicated herein is degree Celsius, unless otherwise explicitly stated. For example, "20 degrees" means "20 degrees Celsius".

Semiconductor Material

The term "semiconductor material" as used in the present invention refers to a material used in a semiconductor manufacturing process. Namely, this term is intended to include, for example, a material forming a coating or layer such as a photoresist coating or underlayer which is removed in the course of a manufacturing process of a circuit. In a preferred aspect of the present invention, the semiconductor material is used in a coating or layer that doses not remain in the semiconductor as a final product. It is desirable that the semiconductor material used as a raw material have an impurity content of 2% or less, preferably 1% or less, more preferably 0.1% or less, further preferably 0.01% or less. Examples of impurities include a starting material for the synthesis process and a precursor remaining unreacted. When the semiconductor material is contained in a composition, the term "impurity content" is used to refer to the amount of impurities relative to the amount of the semiconductor material, and the preferred range of the impurity content is as indicated above.

The semiconductor material according to the present invention consists of a compound represented by formula (1).

[Formula i]

$$X—Y \quad (1)$$

wherein X is a group represented by formula (2).

[Formula ii]

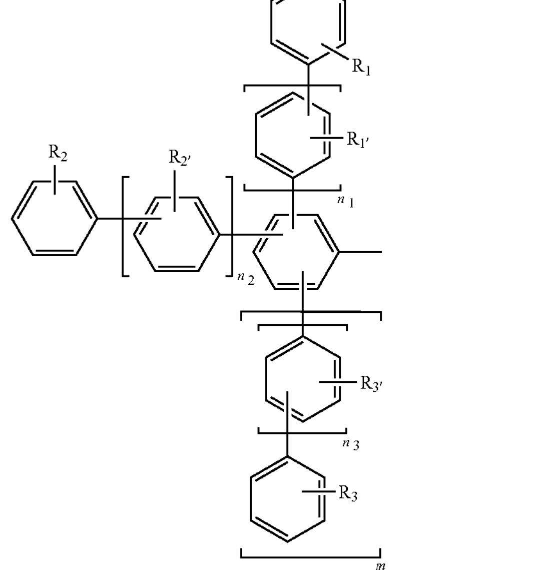

Y is an aromatic hydrocarbon ring unsubstituted or substituted by one or more substituents selected from —OH, —$NH_2$, —SH, linear $C_{1-10}$ alkyl, or branched $C_{3-10}$ alkyl. Preferably, Y is an unsubstituted aromatic hydrocarbon ring or an aromatic hydrocarbon ring substituted by —OH or —$NH_2$. Examples of the aromatic hydrocarbon ring denoted by Y include a monocyclic aromatic hydrocarbon, a compound composed of monocyclic aromatic hydrocarbons linked to each other, and a fused aromatic hydrocarbon. For example, in an aspect, Y is naphthyl substituted by two —OH substituents.

A is —OH, —$NH_2$, or —SH. A is preferably —OH or —$NH_2$ and more preferably —OH. The group denoted by A is thought to contribute to the solubility of the semiconductor material.

$R_1$ is hydrogen, —OH, —$NH_2$, —SH, linear $C_{1-10}$ alkyl, branched $C_{3-10}$ alkyl, or a direct bond to a phenyl ring. $R_1$ is preferably hydrogen, —OH, —$NH_2$, or a direct bond to a phenyl ring, more preferably hydrogen or a direct bond to a phenyl ring, and further preferably hydrogen.

$R_{1'}$ is hydrogen, —OH, —$NH_2$, —SH, linear $C_{1-10}$ alkyl, branched $C_{3-10}$ alkyl, or a direct bond to a phenyl ring. $R_{1'}$ is preferably hydrogen, —OH, —$NH_2$, or a direct bond to a phenyl ring, more preferably hydrogen or a direct bond to a phenyl ring, and further preferably hydrogen.

$R_2$ is hydrogen, —OH, —$NH_2$, —SH, linear $C_{1-10}$ alkyl, branched $C_{3-10}$ alkyl, or a direct bond to a phenyl ring. $R_2$ is preferably hydrogen, —OH, —$NH_2$, or a direct bond to a phenyl ring, more preferably hydrogen, —OH, or a direct bond to a phenyl ring, further preferably hydrogen or —OH, and further more preferably —OH.

$R_{2'}$ is hydrogen, —OH, —$NH_2$, —SH, linear $C_{1-10}$ alkyl, branched $C_{3-10}$ alkyl, or a direct bond to a phenyl ring. $R_{2'}$ is preferably hydrogen, —OH, —$NH_2$, or a direct bond to a phenyl ring, more preferably hydrogen, —OH, or a direct bond to a phenyl ring, and further preferably hydrogen or —OH.

$R_3$ is hydrogen, —OH, —$NH_2$, —SH, linear $C_{1-10}$ alkyl, branched $C_{3-10}$ alkyl, or a direct bond to a phenyl ring. $R_3$ is preferably hydrogen, —OH, —$NH_2$, or a direct bond to a phenyl ring, more preferably hydrogen, —OH, or a direct bond to a phenyl ring, and further preferably hydrogen.

$R_{3'}$ is hydrogen, —OH, —$NH_2$, —SH, linear $C_{1-10}$ alkyl, branched $C_{3-10}$ alkyl, or a direct bond to a phenyl ring. $R_{3'}$ is preferably hydrogen, —OH, —$NH_2$, or a direct bond to a phenyl ring, more preferably hydrogen or a direct bond to a phenyl ring, and further preferably hydrogen.

$n_1$ is 0, 1, or 2. $n_1$ is preferably 0 or 1 and more preferably 0.

$n_2$ is 0, 1, or 2. $n_2$ is preferably 0 or 1 and more preferably 0.

$n_3$ is 0, 1, or 2. $n_3$ is preferably 0 or 1 and more preferably 0.

m is 0, 1, 2, or 3. m is preferably 1, 2, or 3 and more preferably 2 or 3. When m is 2 or 3, plural $R_3$s may be the same as or different from each other and are preferably the same as each other, plural $R_{3'}$s may be the same as or different from each other and are preferably the same as each other, and plural $n_3$s may be the same as or different from each other and are preferably the same as each other.

In terms of synthesis route, it is preferable that one or two monocyclic aromatic hydrocarbons to which A, $R_2$, and/or $R_3$ is attached be bonded to the phenyl bonded to Y and centered in formula (2) at the ortho-position with respect to the linker to Y. More preferably, two monocyclic aromatic hydrocarbons to which A, $R_2$, and/or $R_3$ is attached are bonded to the central phenyl at the ortho-position.

In formula (1), Y is preferably represented by formula (3), (4), (5), or (6).

[Formula iii]

(3)

—L

[Formula iv]

(4)

—L—X

[Formula v]

(5)

—L—L—X

[Formula vi]

(6)

$$\begin{array}{l} —L—X \\ \quad | \\ \quad X \end{array}$$

wherein L is a group represented by formula (7).

[Formula vii]

(7)

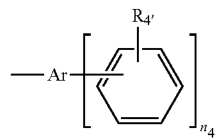

Ar is a $C_{6-20}$ aromatic hydrocarbon ring unsubstituted or substituted by a substituent. Ar is preferably a $C_{6-12}$ aromatic hydrocarbon ring. The substituent is —OH, —$NH_2$, —SH, linear $C_{1-10}$ alkyl, or branched $C_{3-10}$ alkyl. Ar is preferably an unsubstituted $C_{6-20}$ aromatic hydrocarbon ring or a $C_{6-20}$ aromatic hydrocarbon ring substituted by —OH or —$NH_2$. Ar is preferably a monocyclic aromatic hydrocarbon (phenyl, $C_6$) or a fused aromatic hydrocarbon ring. The fused aromatic hydrocarbon ring is preferably naphthyl, phenalene, anthracene, phenanthrene, triphenylene, pyrene, chrysene, or tetracene, more preferably naphthyl or anthracene, and further preferably anthracene. In a preferred aspect of the present invention, Ar is phenyl or anthracene. In a more preferred aspect, Ar is phenyl.

$R_{4'}$ is hydrogen, —OH, —$NH_2$, —SH, linear $C_{1-10}$ alkyl, branched $C_{3-10}$ alkyl, or a direct bond to a phenyl ring. $R_{4'}$ is preferably hydrogen, —OH, —$NH_2$, or a direct bond to a phenyl ring, more preferably hydrogen, —OH, or a direct bond to a phenyl ring, and further preferably hydrogen or —OH.

$n_4$ is 0, 1, 2, 3, or 4. $n_4$ is preferably 0 or 1 and more preferably 0. When $n_4$ is more than 1 (2, 3, or 4) and plural phenyls to which $R_{4'}$ is attached are present in formula (7), each of the phenyls is bonded to Ar in a preferred aspect, while in another preferred aspect, one of the phenyls is bonded to Ar and another of the phenyls is bonded to the one phenyl to form biphenyl. When $n_4$ is more than 1, it is more preferable that each of the phenyls to which $R_{4'}$ is attached be bonded to Ar in formula (7), as in the compound shown below on the left. An example of the compound according to the other aspect in which one of the phenyls is bonded to Ar and another of the phenyls is bonded to the one phenyl is the compound shown below on the right.

[Formula xiv]

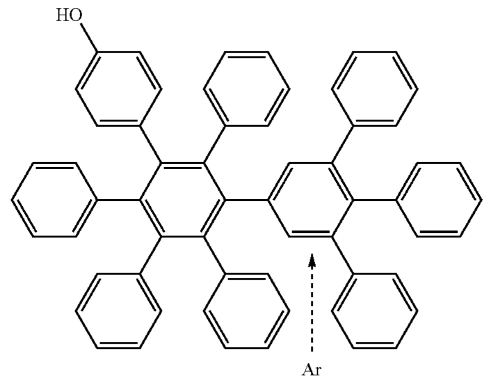

-continued

[Formula xv]

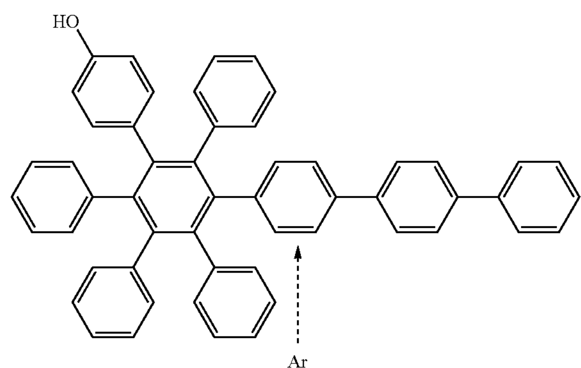

In the formula (3), (4), (5), or (6), the linkers between L and one or more X are each derived from Ar. In formula (5), the linkers between one L and the other L are each derived from Ar. X is as defined above, and preferred examples of X are as described above. Plural Xs in formula (1) may be the same as or different from each other and are preferably the same as each other. In a preferred aspect of the semiconductor material, Y is represented by formula (4).

When the compound of formula (4), (5), or (6) is a symmetrical compound, there is an advantage in that the number of synthesis steps is small. When the compound of formula (4), (5), or (6) is asymmetrical, there is an advantage in that the resulting coating is amorphous and has higher heat resistance. The compound of formula (4) can have a structure bilaterally symmetrical or asymmetrical with respect to L (more preferably Ar) present between two X. The compound of formula (5) can have a structure bilaterally symmetrical or asymmetrical with respect to the center between two L. The compound of formula (6) can have a structure point-symmetrical or point-asymmetrical with respect to L (more preferably Ar) surrounded by three X.

The total number of carbon atoms in the compound of formula (1) according to the present invention is preferably 42-120, more preferably 50-100, further preferably 60-90, and further more preferably 66-84.

In a preferred aspect, L is a group represented by formula (12).

[Formula xvi]

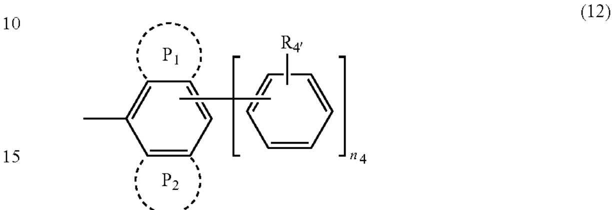

At least one of $P_1$ and $P_2$ each surrounded by the broken line forms an aromatic hydrocarbon ring fused with the adjacent phenyl, or both $P_1$ and $P_2$ form nothing. $R_{4'}$ and $n_4$ are as defined above, and preferred examples of $R_{4'}$ and $n_4$ are as described above. The entire aromatic hydrocarbon ring containing $P_1$ or $P_2$ corresponds to Ar in formula (7). Thus, it is not necessarily the case that the phenyl to which $R_{4'}$ is attached be bonded to phenyl of the aromatic hydrocarbon ring, and the phenyl to which $R_{4'}$ is attached may be bonded to the ring $P_1$ or $P_2$. Preferably, the phenyl to which $R_{4'}$ is attached is bonded to the phenyl to which $P_1$ or $P_2$ is attached in the aromatic hydrocarbon ring. The same applies to formulae (16), (18), and (20) described later.

For example, the group shown below on the left is an example of L, in which both $P_1$ and $P_2$ are phenyl rings and are fused with the adjacent phenyl to form an anthracene ring together. The group shown below on the right is also an example of L, in which both $P_1$ and $P_2$ form nothing. In both the group shown below on the left and the group shown below on the right, $R_{4'}$ is hydrogen and $n_4$ is 1.

[Formula xvii]

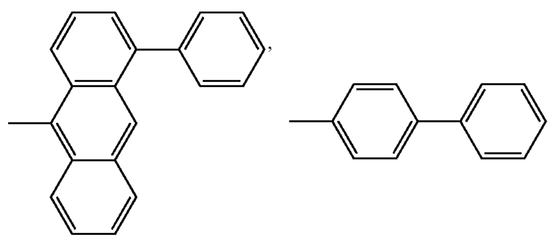

The compound of formula (1) is preferably represented by formula (8), (9), (10), or (11).

[Formula viii]
(8)
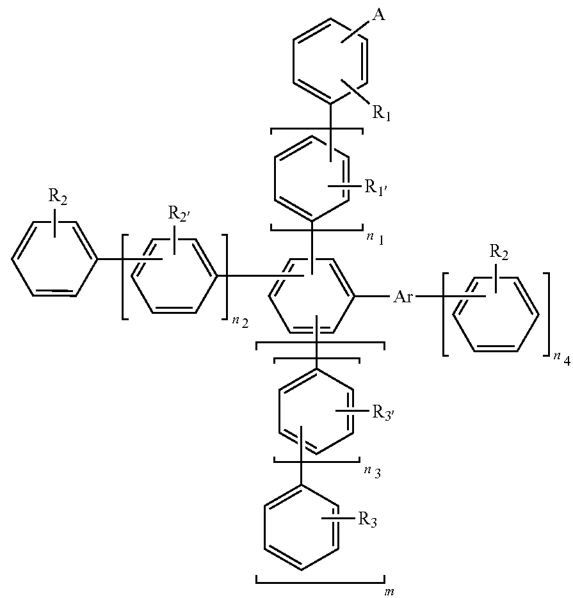
[Formula ix]
(9)
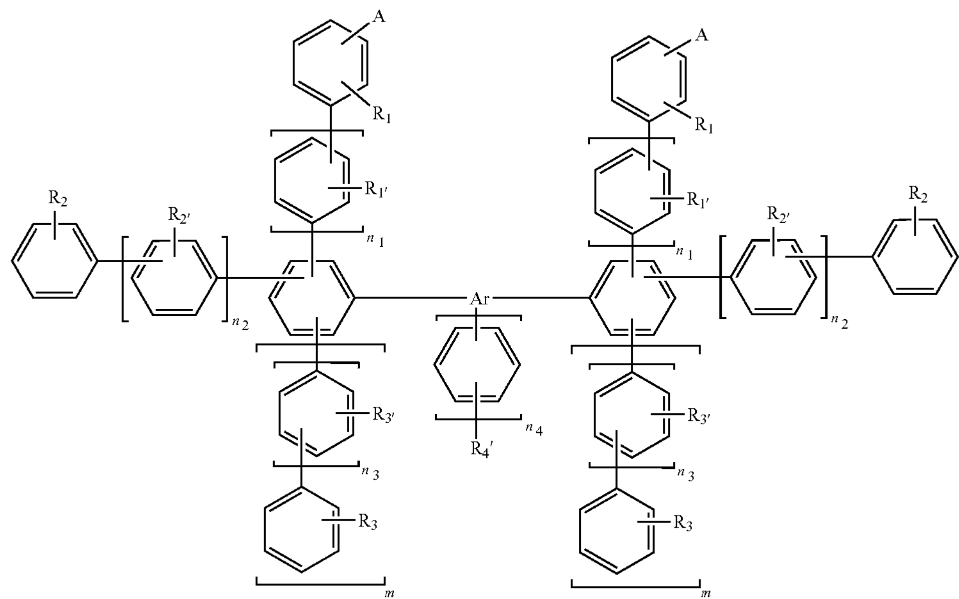

-continued

[Formula x]

(10)

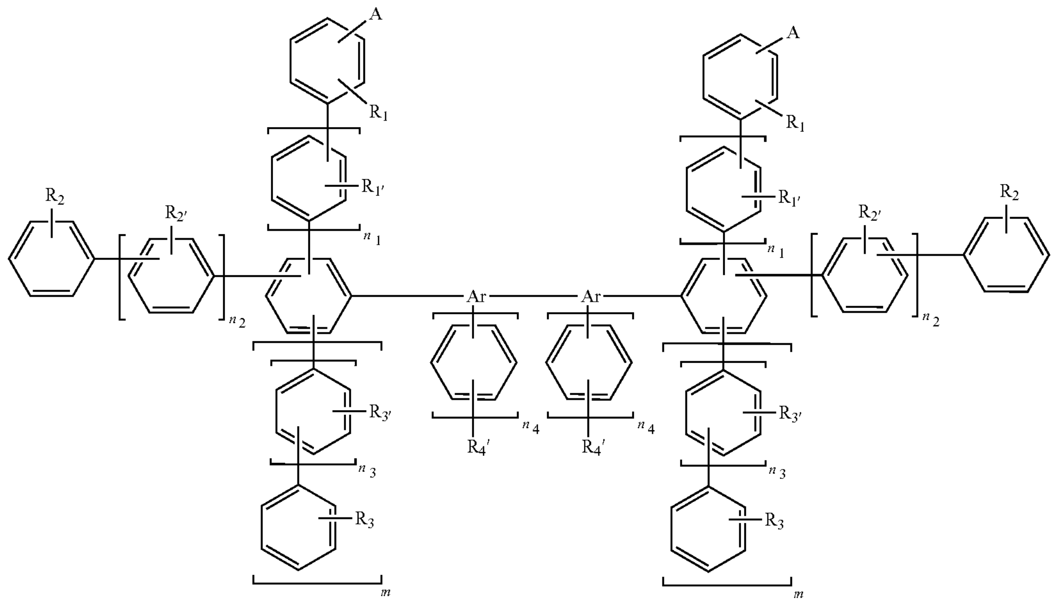

[Formula xi]

(11)

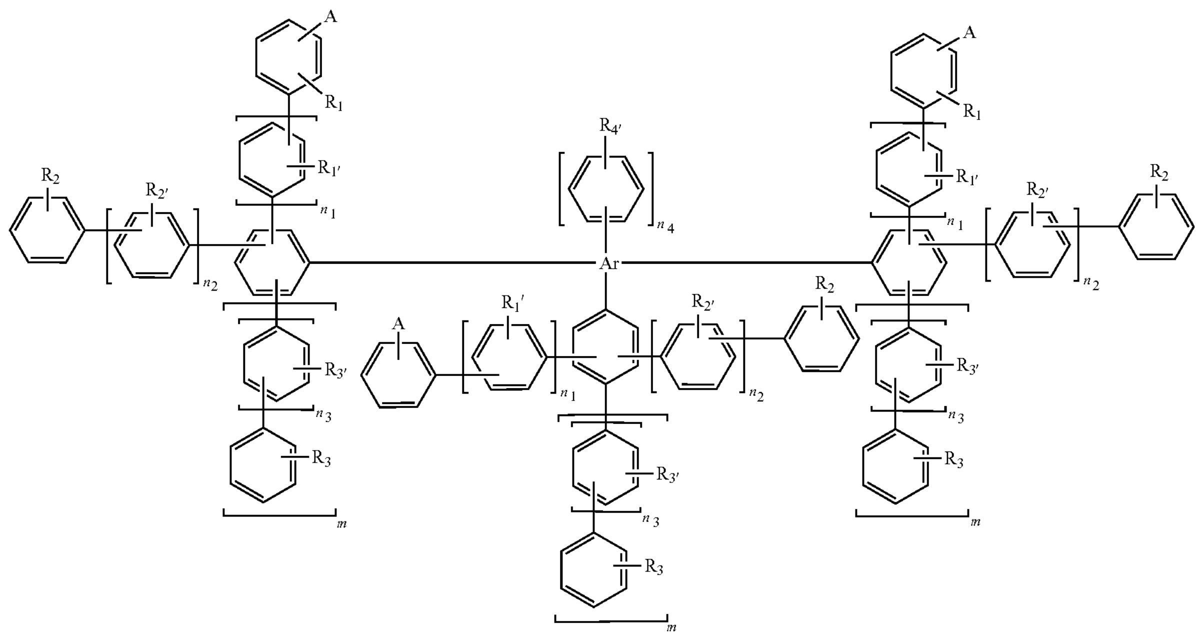

In formulae (8), (9), (10), and (11), A, $R_1$, $R_{1'}$, $R_2$, $R_{2'}$, $R_3$, $R_{3'}$, $n_1$, $n_2$, $n_3$, m, Ar, $R_{4'}$, and $n_4$ are each independently as defined above, and preferred examples of A, $R_1$, $R_{1'}$, $R_2$, $R_{2'}$, $R_3$, $R_{3'}$, $n_1$, $n_2$, $n_3$, m, Ar, $R_{4'}$, and $n_4$ are as described above.

When a plurality of A, $R_1$, $R_{1'}$, $R_2$, $R_{2'}$, $R_3$, $R_{3'}$, $n_1$, $n_2$, $n_3$, m, Ar, $R_{4'}$, or $n_4$ are present in formula (8), (9), (10), or (11), the plurality of A, $R_1$, $R_{1'}$, $R_2$, $R_{2'}$, $R_3$, $R_{3'}$, $n_1$, $n_2$, $n_3$, m, Ar, $R_{4'}$, or $n_4$ may be the same as or different from each other and are preferably the same as each other.

Saying that $R_1$, $R_{1'}$, $R_2$, $R_{2'}$, $R_3$, $R_{3'}$, or $R_4$ is a "direct bond to a phenyl ring" in the present invention means that phenyls are bonded directly to each other without any other linker in formula (2). That is, the term "direct bond to a phenyl ring" does not include a bond between phenyl rings via alkylene as observed in the 9-position of fluorene. The presence of the direct bond to a phenyl ring increases the planarity of the molecule of formula (1).

For example, in a compound of formula (1) which is shown below, Y is represented by formula (4) (-L-X) and A in formula (2) is —OH. The phenyl to which A is attached is bonded to L (phenyl) at the ortho-position. $R_1$, $R_3$, $R_{1'}$, $R_{2'}$, and $R_{3'}$ are each hydrogen, m is 3, and $n_1$, $n_2$, and $n_3$ are each 0. $R_2$ is a direct bond to a phenyl ring. In formula (7), Ar is unsubstituted phenylene ($C_6$), $R_{4'}$ is hydrogen, and $n_4$ is 0. Two X are the same as each other.

[Formula xviii]
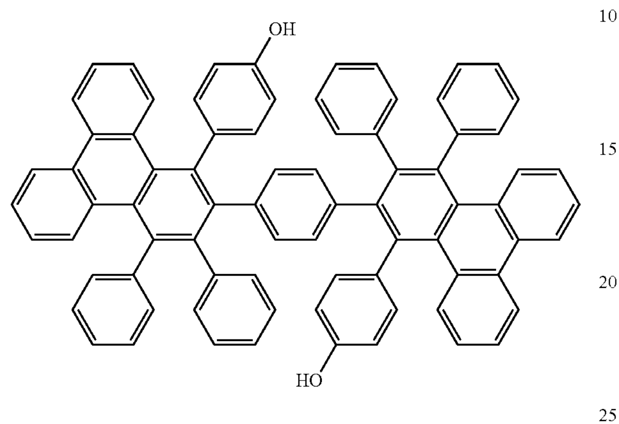
The compound of formula (1) is more preferably represented by formula (13), (14), (15), (16), (17), (18), (19), or (20).
[Formula xix]
(13)
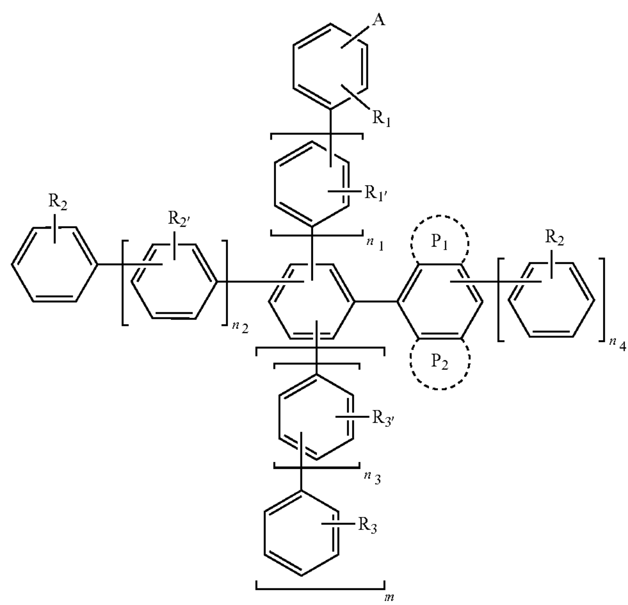

-continued
[Formula xx]
(14)
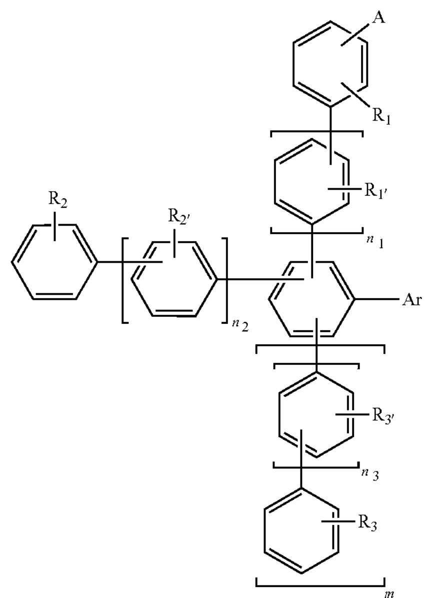
[Formula xxi]
(15)
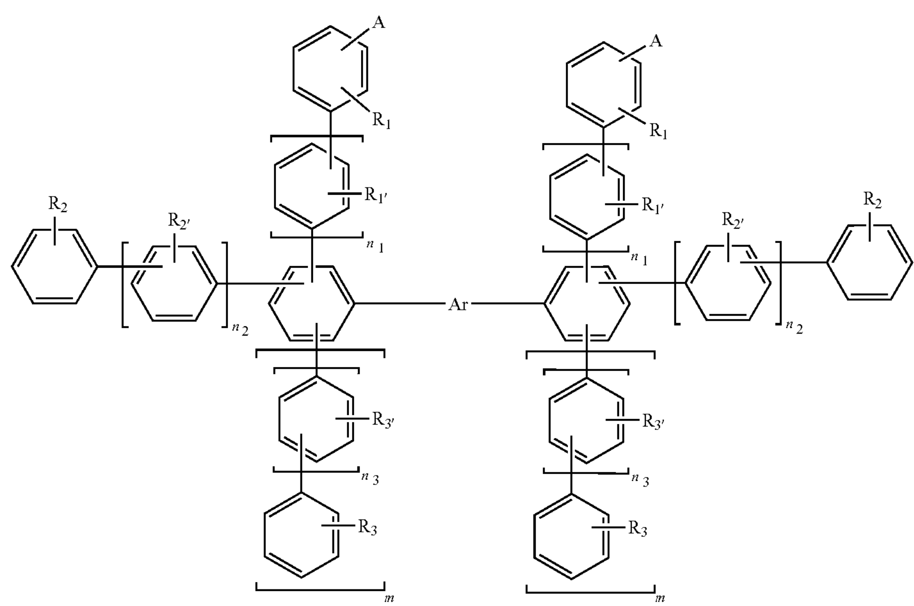

-continued
[Formula xxii]
(16)
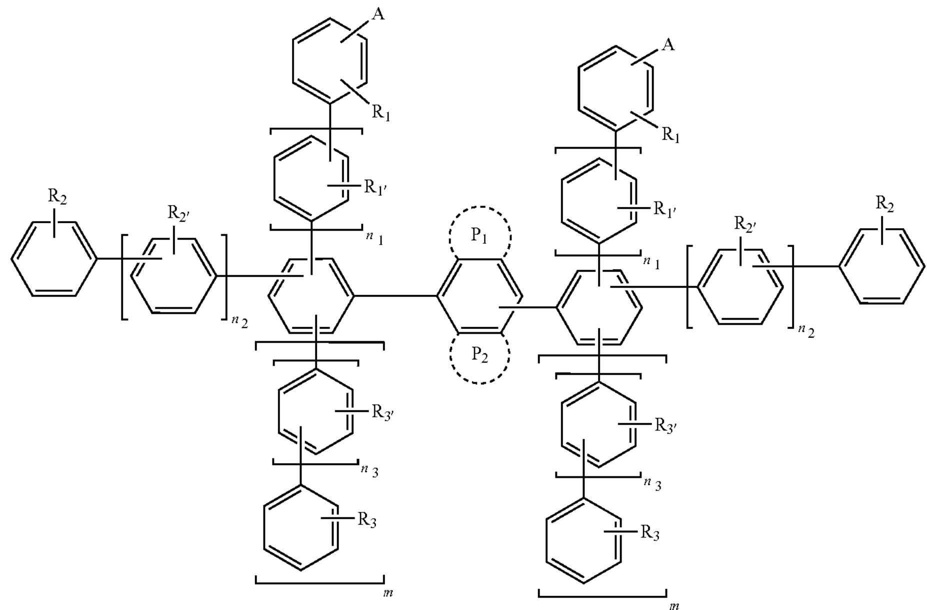
[Formula xxiii]
(17)
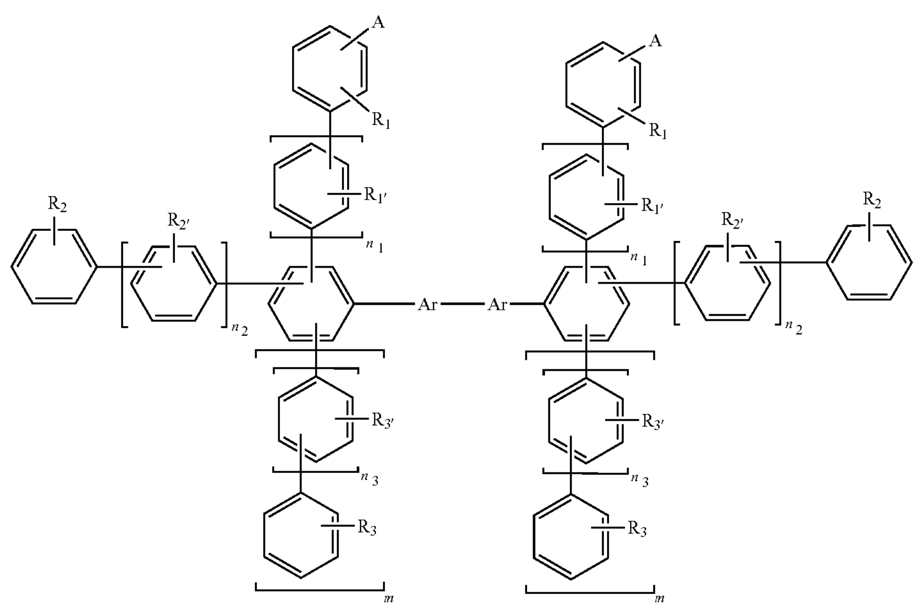

-continued
[Formula xxiv]
(18)
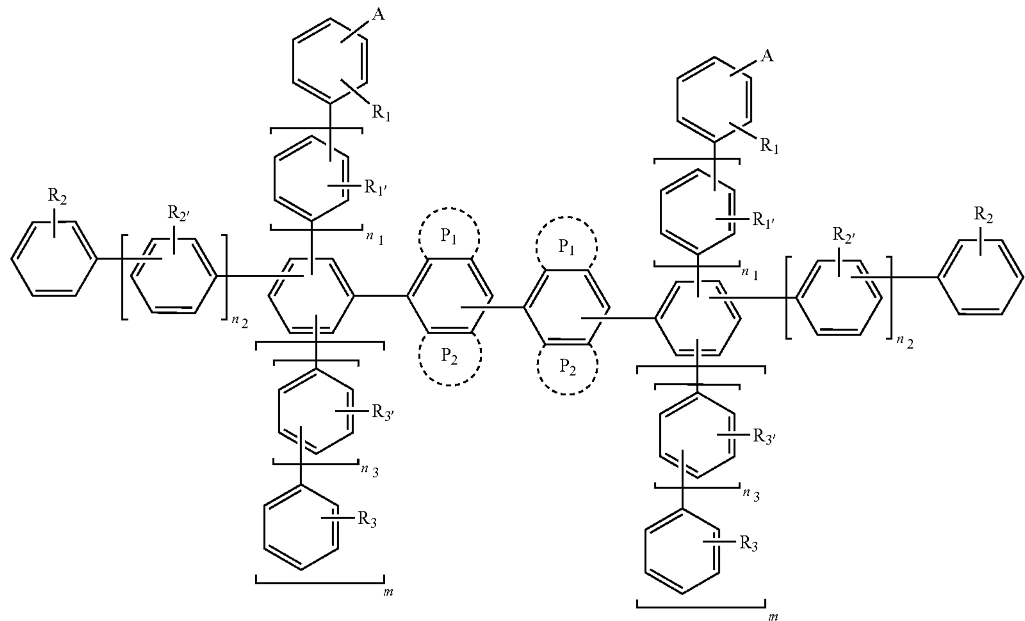
[Formula xxv]
(19)
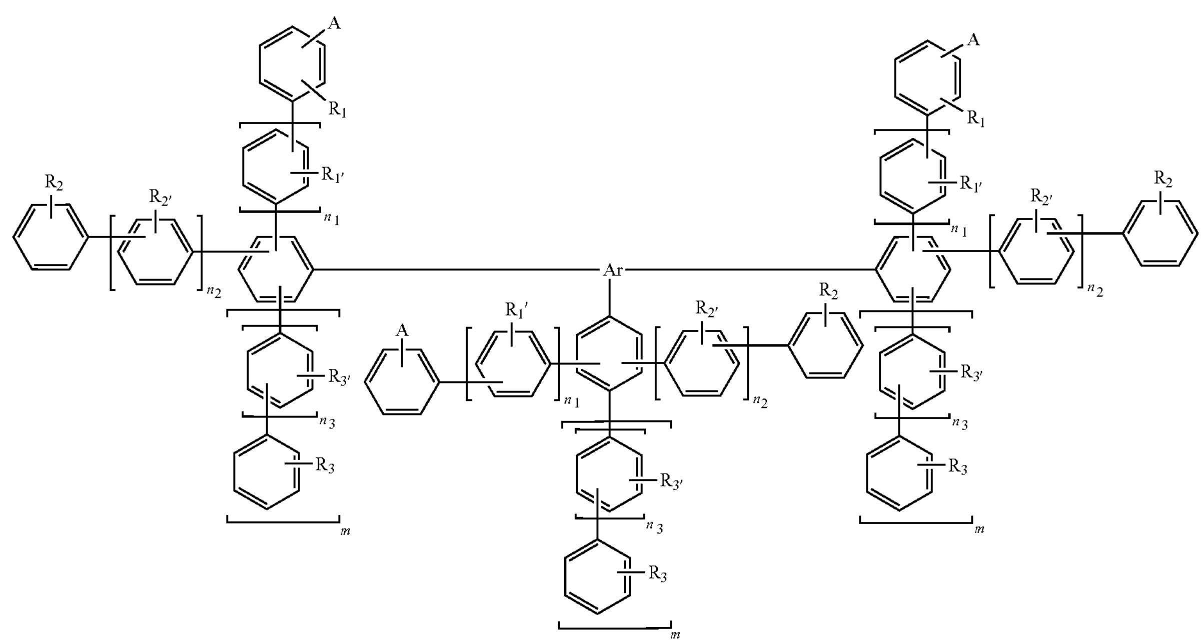

-continued

[Formula xxvi]

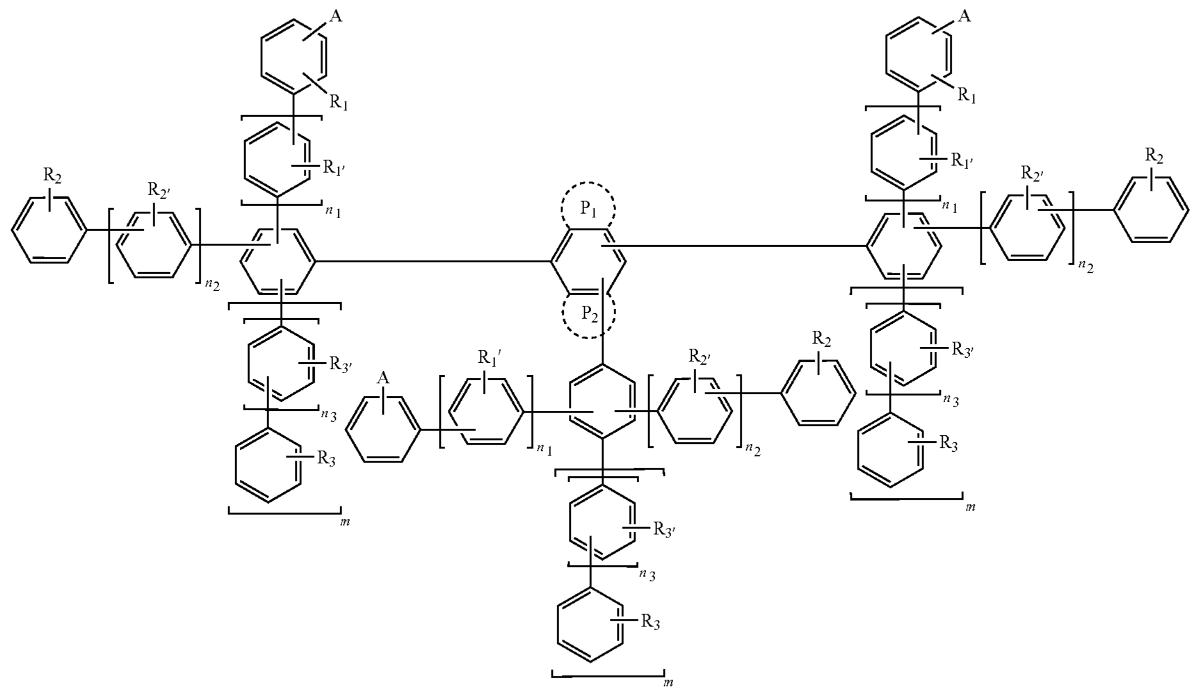

In formulae (13), (14), (15), (16), (17), (18), (19), and (20), A, $R_1$, $R_{1'}$, $R_2$, $R_{2'}$, $R_3$, $R_{3'}$, $n_1$, $n_2$, $n_3$, m, Ar, $R_{4'}$, $n_4$, $P_1$, and $P_2$ are each independently as defined above, and preferred examples of A, $R_1$, $R_{1'}$, $R_2$, $R_{2'}$, $R_3$, $R_{3'}$, $n_1$, $n_2$, $n_3$, m, Ar, $R_{4'}$, $n_4$, $P_1$, and $P_2$ are as described above.

When a plurality of A, $R_1$, $R_{1'}$, $R_2$, $R_{2'}$, $R_3$, $R_{3'}$, $n_1$, $n_2$, $n_3$, m, Ar, $R_{4'}$, $n_4$, $P_1$, or $P_2$ are present in formula (13), (14), (15), (16), (17), (18), (19), or (20), the plurality of A, $R_1$, $R_{1'}$, $R_2$, $R_{2'}$, $R_3$, $R_{3'}$, $n_1$ $n_2$, $n_3$, m, Ar, $R_{4'}$, $n_4$, $P_1$, or $P_2$ may be the same as or different from each other and are preferably the same as each other.

In a more preferred aspect, the compound of formula (1) is a compound represented by formula (15).

The compound represented by formula (1) contains a large number of carbon atoms in total due to being composed of monocyclic aromatic hydrocarbons linked to each other, and further has the group A. This is thought to allow the compound to have advantageous properties for use in a semiconductor material, namely, high etching resistance and high solubility in solvents.

Exemplified embodiments of the compound represented by formula (1) are shown below for illustrative purpose, but are not intended to limit the scope of the present invention.

[Formula xxvii]

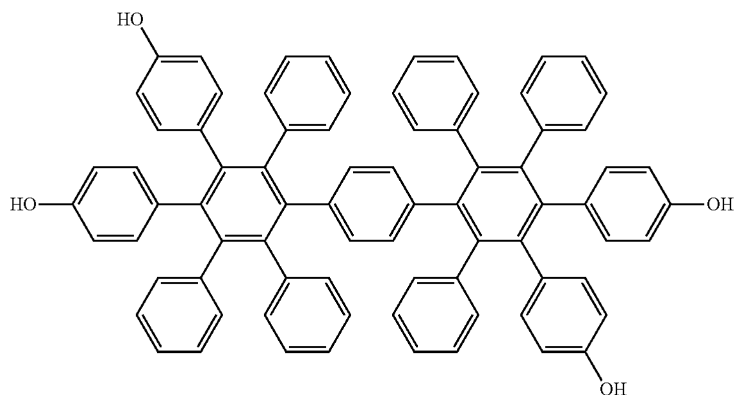

-continued
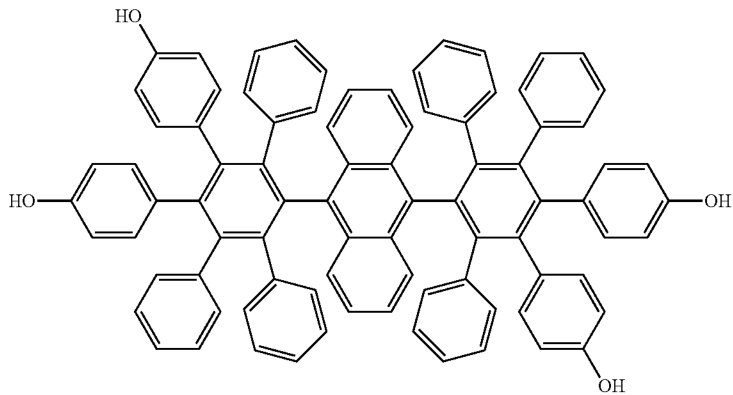
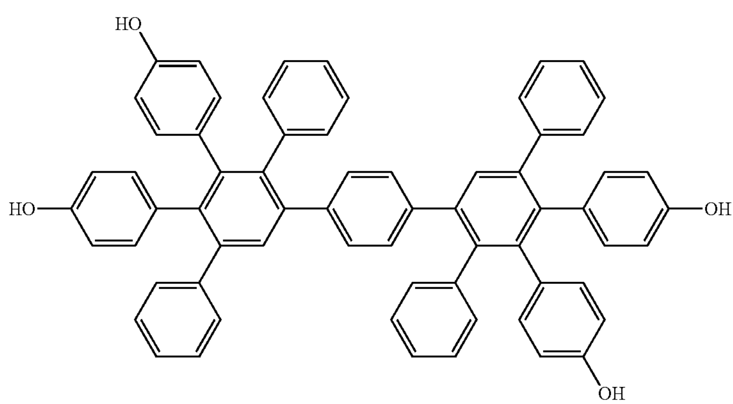
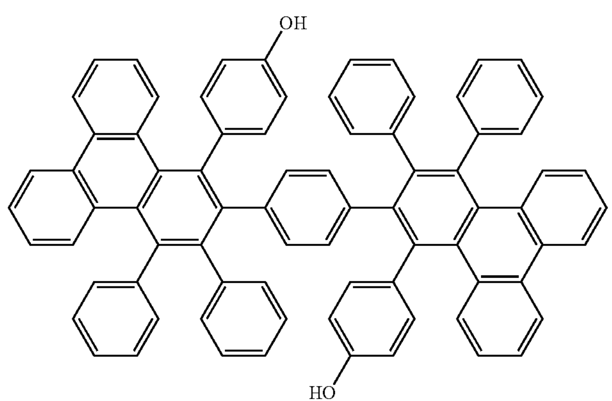

-continued
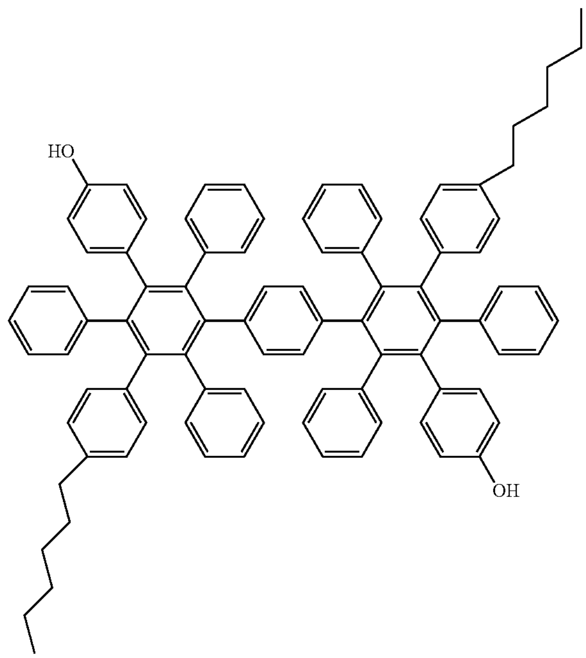
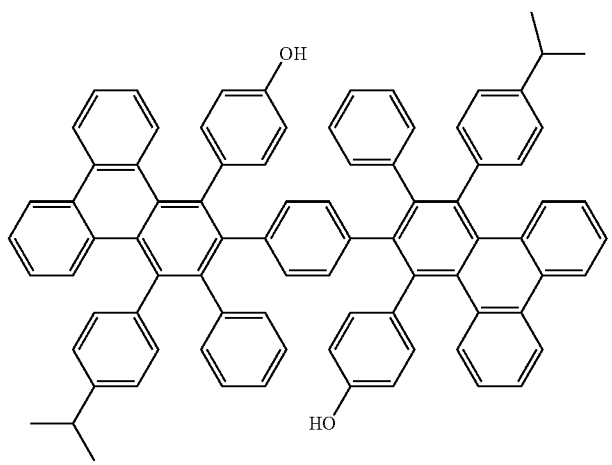
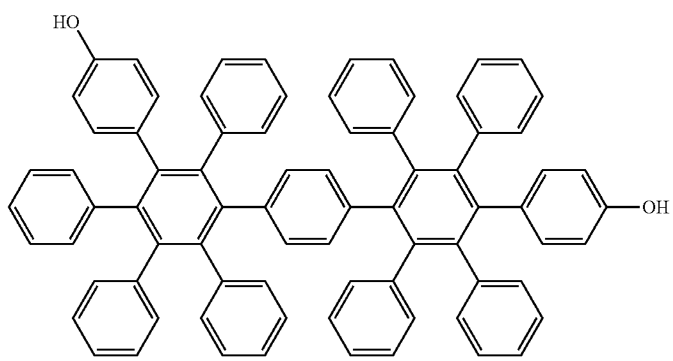
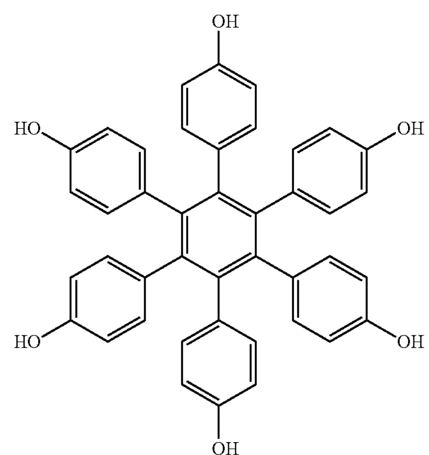

-continued
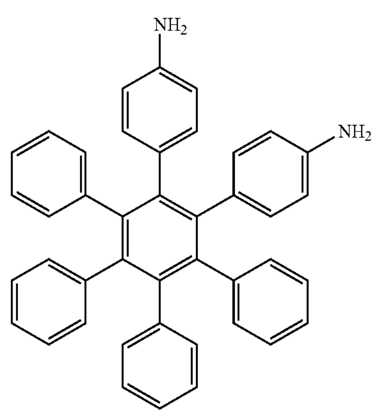
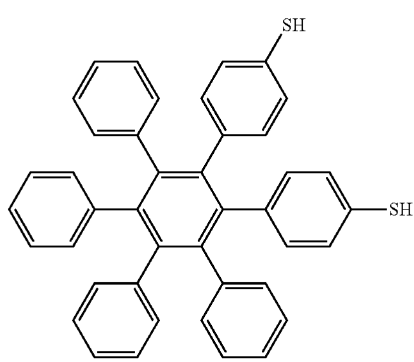
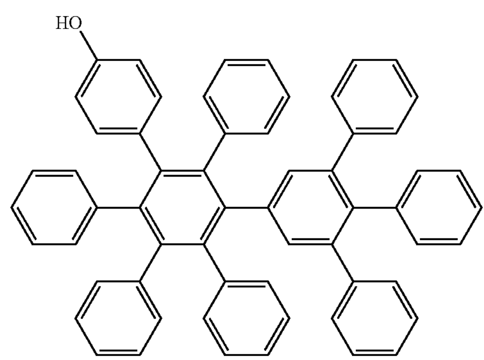
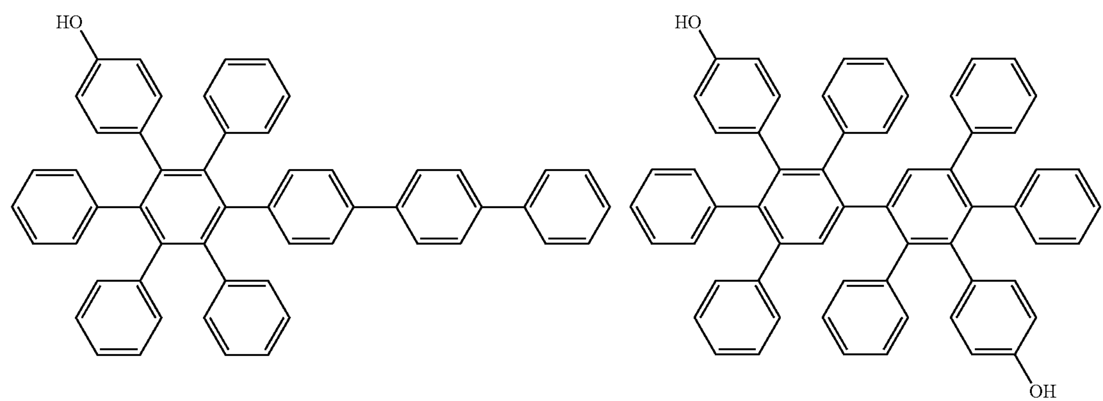

-continued
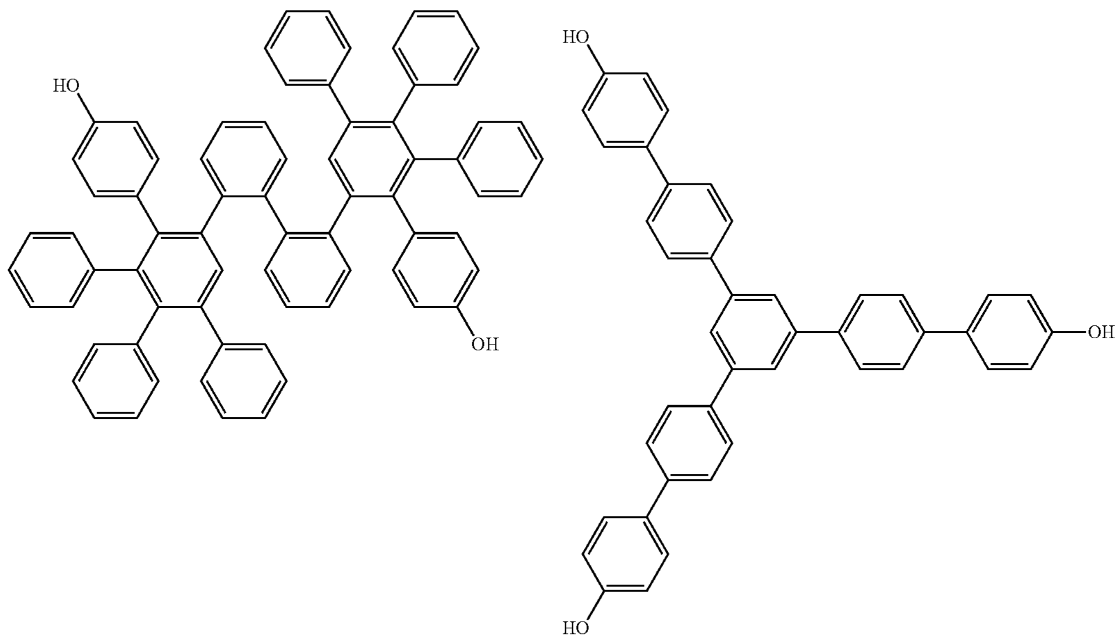
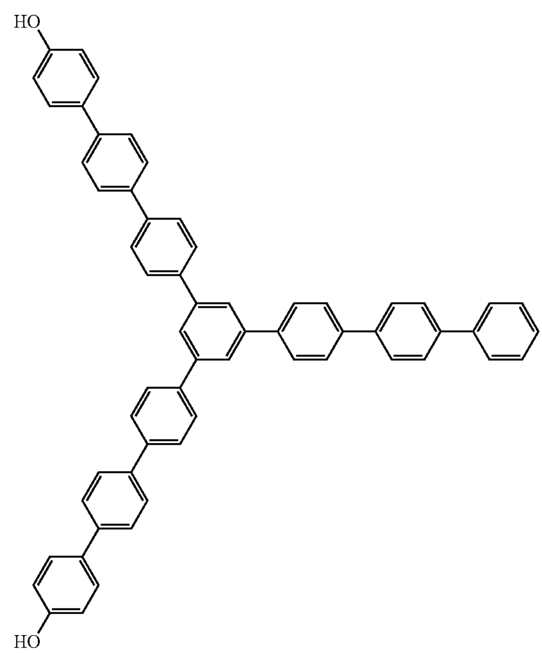

-continued

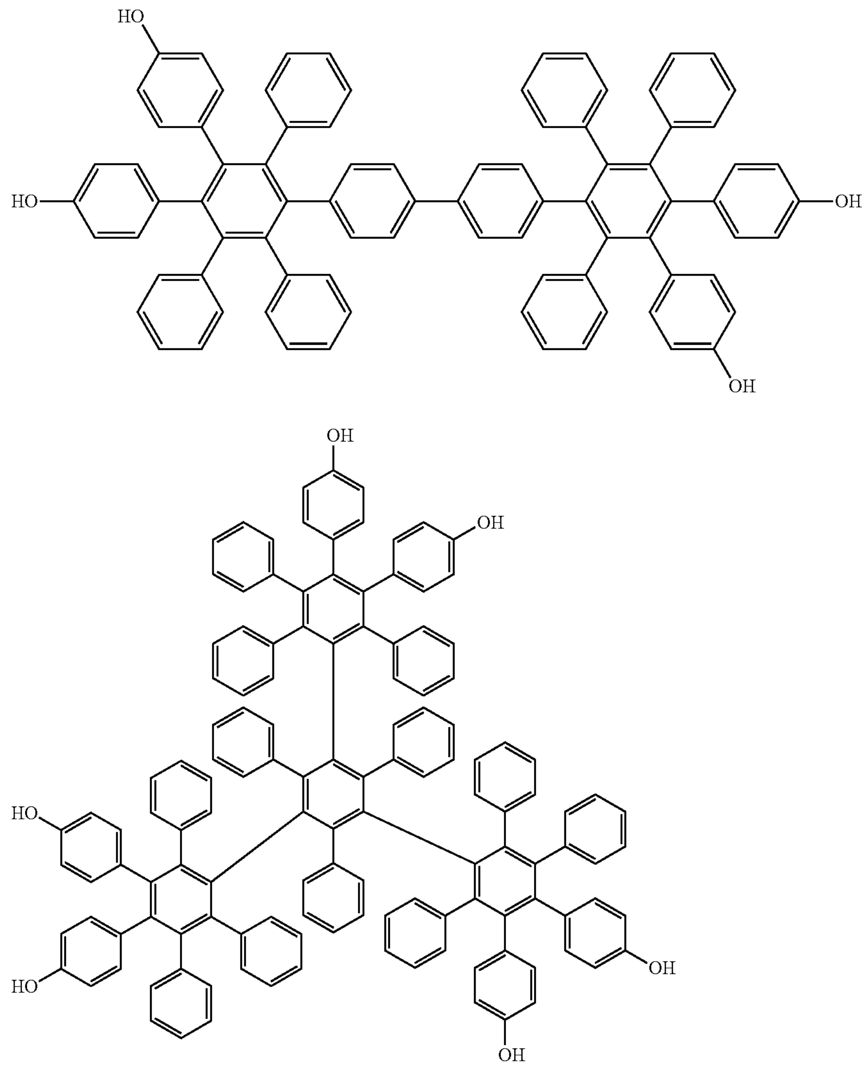

Method for Synthesizing Semiconductor Material of Formula (1)

Detailed procedures of the method for synthesizing the semiconductor material of formula (1) are as described in Synthesis Examples given below. Alternatively, the semiconductor material according to the present invention may be obtained by adding the group A to a precursor or synthetic as described in Non Patent Literature 1, Non Patent Literature 2, or Patent Literature 1. Alternatively, the semiconductor material according to the present invention may be obtained by synthesizing an intermediate having an added methoxy group as described in Synthesis Examples below and by substituting the methoxy group by the group A.

A semiconductor material of formula (8) can be synthesized by the following synthesis method. Cyclopentan-2,4-dienone and acetylene are reacted to form the central phenyl group in X. A substituent (such as phenyl groups in the bracket with a subscript "m") can be introduced into the central phenyl in X by adding the substituent to the acetylene.

[Formula xxviii]

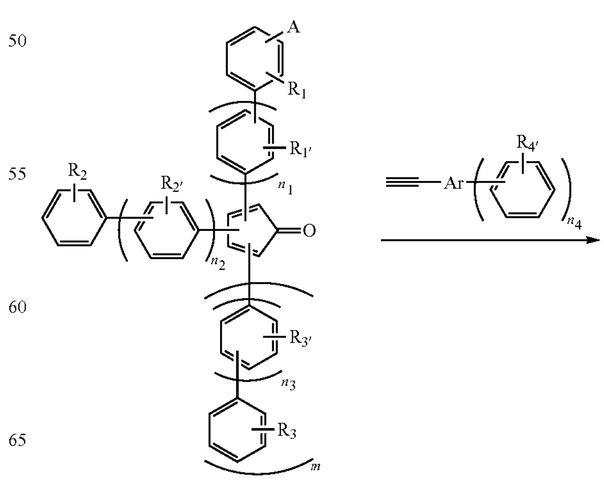

-continued
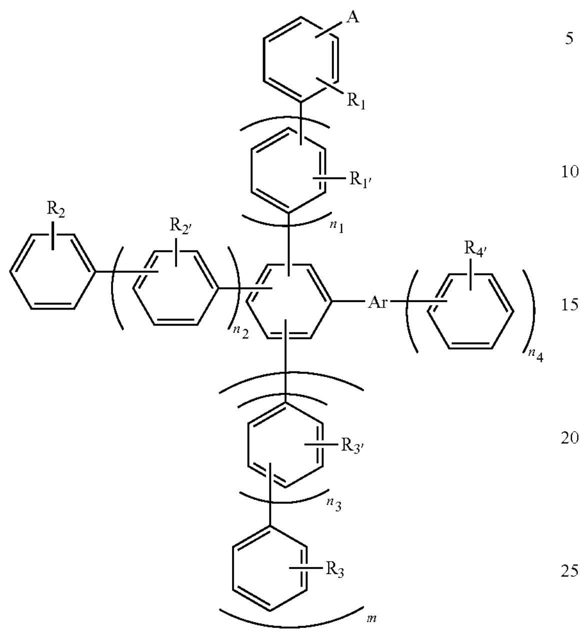
Semiconductor materials of formulae (9), (10), and (11) can be synthesized by changing the intermediate or the amounts of the materials in the above synthesis route. A compound of formula (9) can be obtained through the following synthesis route in which two acetylenes are attached to Ar and the amount of X to be reacted is doubled.
Formula (xxix)
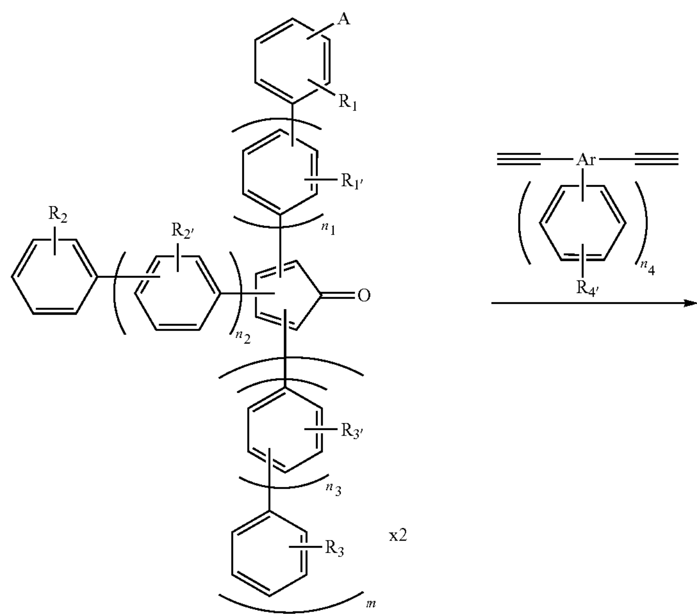

-continued

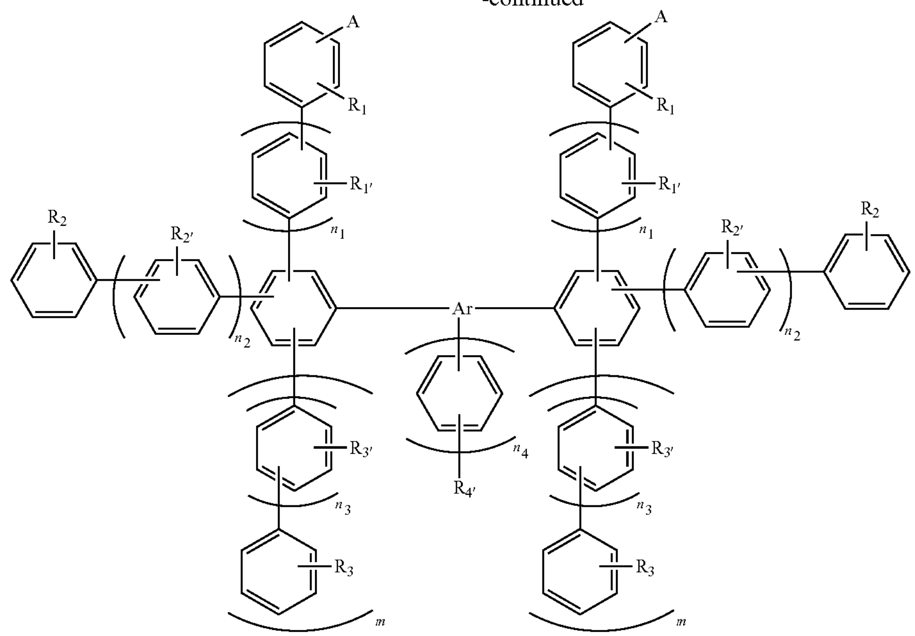

Similarly, a compound of formula (11) can be obtained by attaching three acetylenes to Ar and trebling the amount of X to be reacted.

A compound of formula (10) can be obtained by producing the following compound as an intermediate and doubling the amount of X to be reacted.

[Formula xxx]

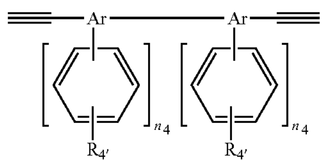

Composition

A composition according to the present invention comprises a semiconductor material of formula (1) and a solvent.

The semiconductor material of formula (1) comprised in the composition is not limited to those consisting of a single compound, and may consist of a combination of plural compounds as long as the compounds are represented by formula (1). For example, both of the following two compounds may be comprised in the composition.

[Formula xxxi]

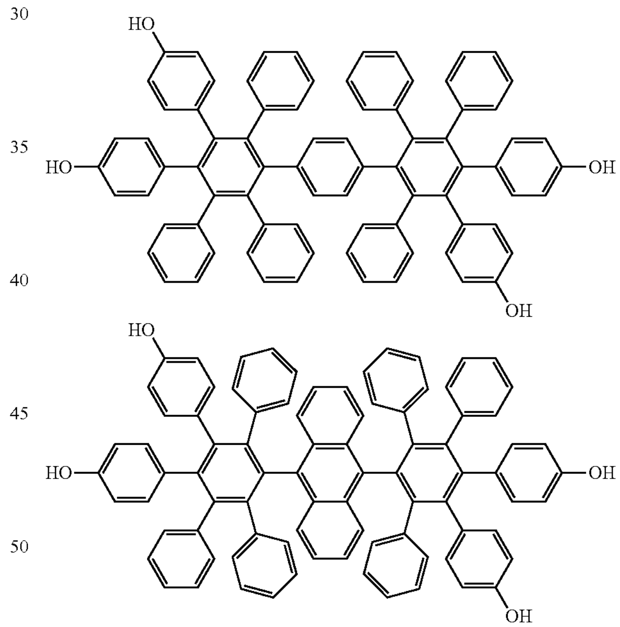

When a combination of the above compounds is used, these compounds may be bonded to each other or reacted independently of each other during coating formation. In the ease of handling during semiconductor manufacturing, the compound of formula (1) comprised in the composition preferably consists of a single compound.

The amount of the semiconductor material of formula (1) is preferably 2-40% by mass, more preferably 2-30% by mass, further preferably 2-20% by mass, and further more preferably 3-10% by mass relative to the total amount of the composition. Increasing the amount of the solid component relative to the total amount of the composition allows formation of a thick coating.

Solid Component Other than Semiconductor Material of Formula (1)

A planarizing coating-forming composition according to the present invention may further comprise a solid component that is other than the semiconductor material of formula (1) and that is formed into a coating. The other solid component may be a low-molecular-weight compound (including a monomer) different from the semiconductor material of formula (1) or may be a polymer. When formed into a coating, the other solid component may be bonded to the semiconductor material of formula (1) or may be reacted independently of the semiconductor material of formula (1). And those states can exist in 1 composition as mixed.

Solvent

The solvent used in the present invention is, for example, water or an organic solvent.

Examples of the organic solvent include: aliphatic hydrocarbon solvents such as n-pentane, i-pentane, n-hexane, i-hexane, n-heptane, i-heptane, 2,2,4-trimethylpentane, n-octane, i-octane, cyclohexane, and methylcyclohexane; aromatic hydrocarbon solvents such as benzene, toluene, xylene, ethylbenzene, trimethylbenzene, methylethylbenzene, n-propylbenzene, i-propylbenzene, diethylbenzene, i-butylbenzene, triethylbenzene, di-i-propylbenzene, n-amylnaphthalene, and trimethylbenzene; monoalcohol solvents such as methanol, ethanol, n-propanol, i-propanol, n-butanol, i-butanol, sec-butanol, t-butanol, n-pentanol, i-pentanol, 2-methylbutanol, sec-pentanol, t-pentanol, 3-methoxybutanol, n-hexanol, 2-methylpentanol, sec-hexanol, 2-ethylbutanol, sec-heptanol, heptanol-3, n-octanol, 2-ethylhexanol, sec-octanol, n-nonyl alcohol, 2,6-dimethylheptanol-4, n-decanol, sec-undecyl alcohol, trimethylnonyl alcohol, sec-tetradecyl alcohol, sec-heptadecyl alcohol, phenol, cyclohexanol, methylcyclohexanol, 3,3,5-trimethylcyclohexanol, benzyl alcohol, phenylmethylcarbinol, diacetone alcohol, and cresol; polyol solvents such as ethylene glycol, propylene glycol, 1,3-butylene glycol, pentanediol-2,4, 2-methylpentanediol-2,4, hexanediol-2,5, heptanediol-2,4, 2-ethylhexanediol-1,3, diethylene glycol, dipropylene glycol, triethylene glycol, tripropylene glycol, and glycerin; ketone solvents such as acetone, methyl ethyl ketone, methyl n-propyl ketone, methyl n-butyl ketone, diethyl ketone, methyl i-butyl ketone, methyl n-pentyl ketone, ethyl n-butyl ketone, methyl n-hexyl ketone, di-i-butyl ketone, trimethylnonanone, cyclohexanone, cyclopentanone, methylcyclohexanone, 2,4-pentanedione, acetonylacetone, diacetone alcohol, acetophenone, and fenchone; ether solvents such as ethyl ether, i-propyl ether, n-butyl ether, n-hexyl ether, 2-ethylhexyl ether, ethylene oxide, 1,2-propylene oxide, dioxolane, 4-methyldioxolane, dioxane, dimethyldioxane, ethylene glycol monomethyl ether, ethylene glycol monoethyl ether, ethylene glycol diethyl ether, ethylene glycol mono-n-butyl ether, ethylene glycol mono-n-hexyl ether, ethylene glycol monophenyl ether, ethylene glycol mono-2-ethylbutyl ether, ethylene glycol dibutyl ether, diethylene glycol monomethyl ether, diethylene glycol monoethyl ether, diethylene glycol diethyl ether, diethylene glycol mono-n-butyl ether, diethylene glycol di-n-butyl ether, diethylene glycol mono-n-hexyl ether, ethoxy triglycol, tetraethylene glycol di-n-butyl ether, propylene glycol monomethyl ether (PGME), propylene glycol monoethyl ether, propylene glycol monopropyl ether, propylene glycol monobutyl ether, dipropylene glycol monomethyl ether, dipropylene glycol monoethyl ether, dipropylene glycol monopropyl ether, dipropylene glycol monobutyl ether, tripropylene glycol monomethyl ether, tetrahydrofuran, and 2-methyltetrahydrofuran; ester solvents such as diethyl carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate, propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, i-amyl propionate, diethyl oxalate, di-n-butyl oxalate, methyl lactate, ethyl lactate (EL), γ-butyrolactone, n-butyl lactate, n-amyl lactate, diethyl malonate, dimethyl phthalate, diethyl phthalate, propylene glycol 1-monomethyl ether 2-acetate (PGMEA), propylene glycol monoethyl ether acetate, and propylene glycol monopropyl ether acetate; nitrogen-containing solvents such as N-methylformamide, N,N-dimethylformamide, N,N-diethylformamide, acetamide, N-methylacetamide, N,N-dimethylacetamide, N-methylpropionamide, and N-methylpyrrolidone; and sulfur-containing solvents such as dimethyl sulfide, diethyl sulfide, thiophene, tetrahydrothiophene, dimethyl sulfoxide, sulfolane, and 1,3-propanesultone. Any mixture of any of these solvents can also be used.

In particular, cyclohexanone, cyclopentanone, propylene glycol monomethyl ether, propylene glycol monoethyl ether, propylene glycol monopropyl ether, propylene glycol monobutyl ether, propylene glycol dimethyl ether, propylene glycol diethyl ether, propylene glycol 1-monomethyl ether 2-acetate, propylene glycol monoethyl ether acetate, propylene glycol monopropyl ether acetate, γ-butyrolactone, ethyl lactate, and any mixture of any of these are preferred in terms of the storage stability of the solution.

In terms of the solubility of the solute, propylene glycol monomethyl ether, propylene glycol 1-monomethyl ether 2-acetate, ethyl lactate, and a mixture of any two solvents selected therefrom are preferred. The mixture of two solvents is preferably a mixture in a volume ratio of 10:90 to 90:10 and more preferably a mixture in a volume ratio of 25:75 to 75:25.

The amount of the one or more organic solvents (or the total amount of the two or more organic solvents) is preferably 60-98% by mass, more preferably 70-98% by mass, and further preferably 80-98% by mass relative to the total amount of the composition. The one or more solvents preferably comprise an organic solvent, and the amount of water in the composition is preferably 0.1% by mass or less and further preferably 0.01% by mass or less. Given the relationship with another layer or coating, it is preferable for the solvents to be free of water. In an aspect of the present invention, the amount of water in the composition is 0.00% by mass.

Surfactant

The composition may further comprise a surfactant, a crosslinking agent, an acid generator, a radical generator, an agent for enhancing the adhesion to substrates, or any combination of any of these.

A surfactant is useful for preventing the occurrence of pinholes, striation or the like and improving the ease of application and solubility of the planarizing coating-forming composition. The amount of the surfactant in the composition is preferably 0.01-5% by mass and more preferably 0.05-3% by mass relative to the total amount of the composition.

Examples of the surfactant include: polyoxyethylene alkyl ether compounds such as polyoxyethylene lauryl ether, polyoxyethylene stearyl ether, and polyoxyethylene oleyl ether; polyoxyethylene alkylaryl ether compounds such as polyoxyethylene octylphenol ether and polyoxyethylene nonylphenol ether; polyoxyethylene-polyoxypropylene block copolymer compounds; sorbitan fatty acid ester compounds such as sorbitan monolaurate, sorbitan monopalmitate, sorbitan monostearate, sorbitan trioleate, and sorbitan tristearate; and polyoxyethylene sorbitan fatty acid ester compounds such as polyoxyethylene sorbitan monolaurate, polyoxyethylene sorbitan monopalmitate, polyoxyethylene sorbitan monostearate, and polyoxyethylene sorbitan tristearate. Other examples of the surfactant include: fluorosurfactants such as EFTOP (trade name) EF301, EF303, and EF352 (manufactured by Tohkem Products Corporation), MEGAFACE (trade name) F171, F173, R-08, R-30, and R-2011 (manufactured by DIC Corporation), Fluorad FC430 and FC431 (manufactured by Sumitomo 3M Limited), AsahiGuard (trade name) AG710 (manufactured by Asahi Glass Co., Ltd.), and SURFLON S-382, SC101, SC102, SC103, SC104, SC105, and SC106 (manufactured by Asahi Glass Co., Ltd.); and organosiloxane polymers such as KP341 (manufactured by Shin-Etsu Chemical Co., Ltd.).

Crosslinking Agent

A crosslinking agent can be added for the purpose of improving the coating formation property of the coating to be formed, preventing intermixing with an upper layer (such as a silicon-containing interlayer and a resist), and preventing diffusion of a low-molecular-weight component into the upper layer.

Exemplified embodiments of crosslinking agents that can be used in the present invention include: melamine, guanamine, glycoluril, and urea compounds substituted by at least one group selected from a methylol group, an alkoxymethyl group, and an acyloxymethyl group; epoxy compounds; thioepoxy compounds; isocyanate compounds; azide compounds; and compounds having a double bond-containing group such as an alkenyl ether group. These may be used as an additive or may alternatively be introduced as a pendant group into a polymer side chain. Compounds containing a hydroxy group can also be used as a crosslinking agent.

Examples of the epoxy compounds mentioned above include tris(2,3-epoxypropyl) isocyanurate, trimethylolmethane triglycidyl ether, trimethylolpropane triglycidyl ether, and triethylolethane triglycidyl ether. Exemplified embodiments of the melamine compounds include hexamethylolmelamine, hexamethoxymethylmelamine, compounds derived by methoxymethylation of 1-6 methylol groups of hexamethylolmelamine, any mixture of any of such compounds, hexamethoxyethylmelamine, hexaacyloxymethylmelamine, compounds derived by acyloxymethylation of 1-6 methylol groups of hexamethylolmelamine, and any mixture of any of such compounds. Examples of the guanamine compounds include tetramethylolguanamine, tetramethoxymethylguanamine, compounds derived by methoxymethylation of 1-4 methylol groups of tetramethylolguanamine, any mixture of any of such compounds, tetramethoxyethylguanamine, tetraacyloxyguanamine, compounds derived by acyloxymethylation of 1-4 methylol groups of tetramethylolguanamine, and any mixture of any of such compounds. Examples of the glycoluril compounds include tetramethylolglycoluril, tetramethoxyglycoluril, tetramethoxymethylglycoluril, compounds derived by methoxymethylation of 1-4 methylol groups of tetramethylolglycoluril, any mixture of any of such compounds, compounds derived by acyloxymethylation of 1-4 methylol groups of tetramethylolglycoluril, and any mixture of any of such compounds. Examples of the urea compounds include tetramethylolurea, tetramethoxymethylurea, compounds derived by methoxymethylation of 1-4 of methylol groups of tetramethylolurea, any mixture of any of such compounds, and tetramethoxyethylurea.

Examples of the compounds containing an alkenyl ether group include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of the crosslinking agent used in the present invention include those represented by formula (21).

[Formula xxxii]

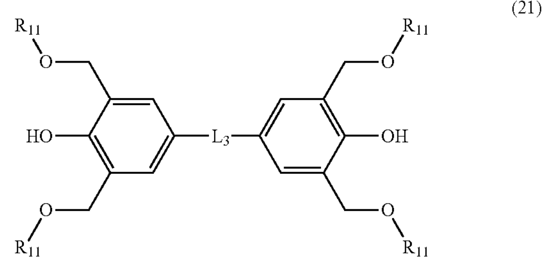

In formula (21), $L_3$ is a direct bond, substituted or unsubstituted $C_{1-3}$ alkyl, or substituted or unsubstituted $C_{7-16}$ aralkyl. $L_3$ is preferably a direct bond, $C_1$ alkyl, or $C_{15}$ aralkyl. The substituent of the alkyl or aralkyl is preferably hydrogen, methyl, $C_{6-11}$ aryl, or a substituent of formula (22) or formula (23) and more preferably methyl or a substituent of formula (22). In a preferred aspect, $L_3$ is unsubstituted $C_{1-3}$ alkyl or unsubstituted $C_{1-3}$ aralkyl.

In formula (21), $R_{11}$ is hydrogen or methyl.

[Formula xxxiii]

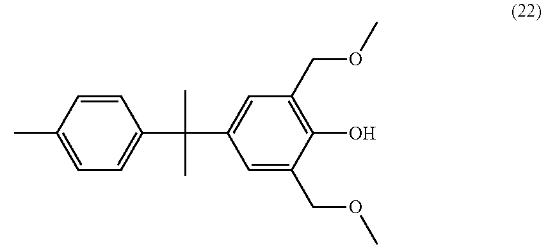

-continued

[Formula xxxiv]

(23)

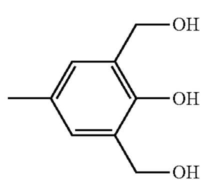

The following are exemplified embodiments of the crosslinking agent represented by formula (21). The scope of the present invention is not limited to them.

[Formula xxxv]

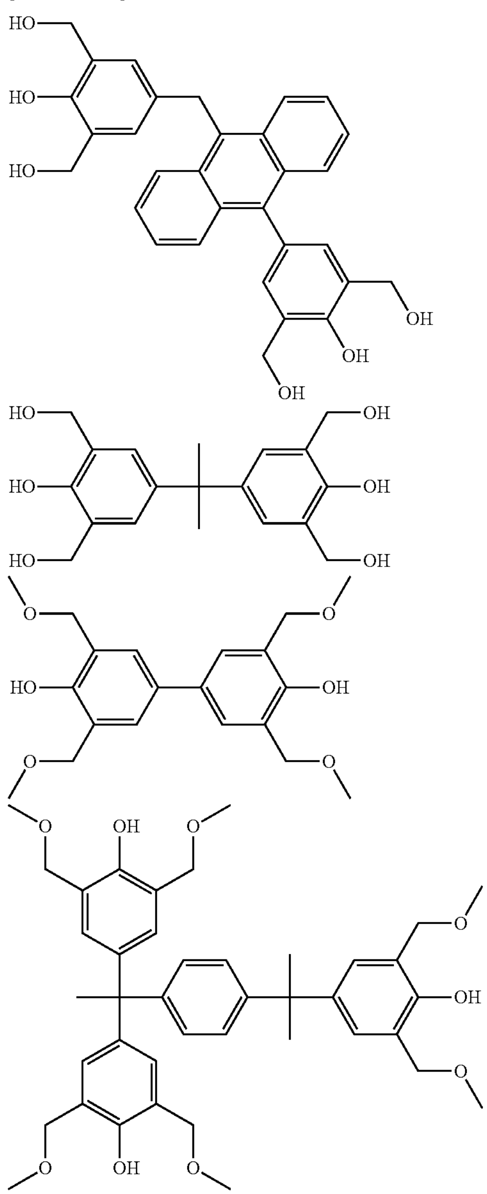

The following are exemplified embodiments of another crosslinking agent that can be contained in the planarizing coating-forming composition. The scope of the present invention is not limited to them.

[Formula xxxvi]

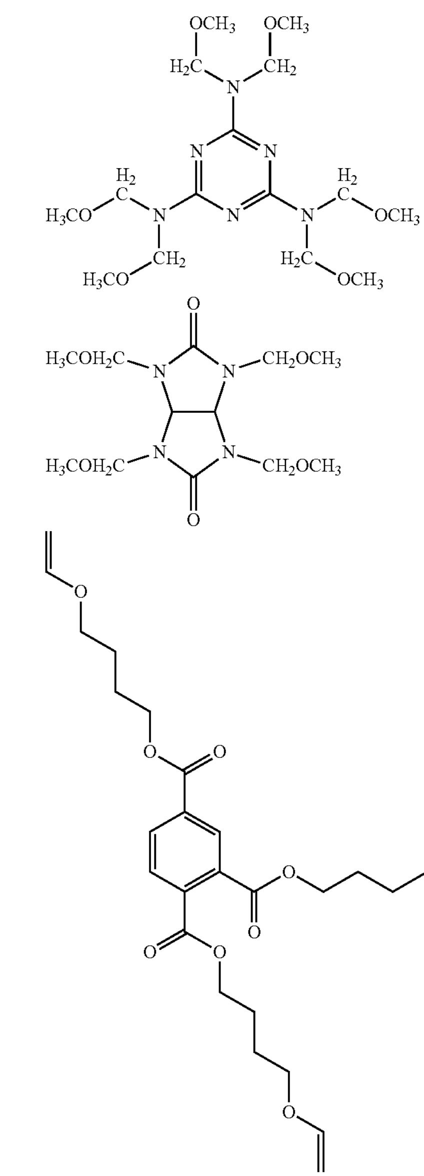

These crosslinking agents are available, for example, from Sanwa Chemical Co., Ltd., Honshu Chemical Industry Co., Ltd., Asahi Yukizai Corporation, and Nippon Carbide Industries Co., Inc.

In the present invention, the amount of the crosslinking agent is preferably 10-100% by mass, more preferably 40-100% by mass, further preferably 50-90% by mass, and further more preferably 70-90% by mass relative to the mass of the semiconductor material of formula (1) (or the total mass of the two or more semiconductor materials of formula (1)) comprised in the composition. The incorporation of the crosslinking agent in the composition is expected to produce the following effect: the crosslinking agent binds to the compound of formula (1) during coating formation to control the intramolecular torsion of the whole composite of the crosslinking agent and the compound and increase the planarity of the composite.

Given the ease of process control, the present invention may be implemented as an embodiment in which the semiconductor material of formula (1) is formed into a coating by itself without addition of the crosslinking agent (this means that the amount of the crosslinking agent is 0% by mass relative to the mass of the semiconductor material of formula (1)).

Acid Generator

The composition according to the present invention may further comprise an acid generator. The amount of the acid generator contained in the composition is preferably 0.1-10% by mass, more preferably 1-7% by mass, and further preferably 1-5% by mass relative to the mass of the semiconductor material of formula (1) (or the total mass of the two or more semiconductor materials of formula (1)).

The acid generator can be a thermal acid generator capable of generating a strong acid when heated. The thermal acid generator (TAG) used in the present invention can comprise one or more thermal acid generators which, when heated, generate an acid capable of reacting with the semiconductor material of formula (I) present in the present invention and capable of promoting crosslinking of the semiconductor material. The acid is more preferably a strong acid such as sulfonic acid. The acid is more preferably a strong acid such as sulfonic acid. The thermal acid generator is preferably activated at a temperature above 80 degrees. Examples of the thermal acid generator include: metal-free sulfonium salts such as triarylsulfonium, dialkylarylsulfonium, and diarylalkylsulfonium salts of strong non-nucleophilic acids; metal-free iodonium salts such as alkylaryliodonium and diaryliodonium salts of strong non-nucleophilic acids; and ammonium, alkylammonium, dialkylammonium, trialkylammonium, and tetraalkylammonium salts of strong non-nucleophilic acids. Covalent thermal acid generators are also considered useful as additives, and examples include 2-nitrobenzyl esters of alkylsulfonic or arylsulfonic acids and other sulfonic acid esters which are thermally decomposed to give free sulfonic acid. Examples thereof include diaryliodonium perfluoroalkyl sulfonates, diaryliodonium tris(fluoroalkylsulfonyl)methides, diaryliodonium bis(fluoroalkylsulfonyl)methides, diaryliodonium bis(fluoroalkylsulfonyl)imides, and diaryliodonium quaternary ammonium perfluoroalkyl sulfonates. Examples of labile esters include: nitrobenzyl tosylates such as 2-nitrobenzyl tosylate, 2,4-dinitrobenzyl tosylate, 2,6-dinitrobenzyl tosylate, and 4-nitrobenzyl tosylate; benzenesulfonates such as 2-trifluoromethyl-6-nitrobenzyl 4-chlorobenzenesulfonate and 2-trifluoromethyl-6-nitrobenzyl 4-nitrobenzenesulfonate; phenolic sulfonate esters such as phenyl 4-methoxybenzenesulfonate; quaternary ammonium tris(fluoroalkylsulfonyl)methides; quaternary alkylammonium bis(fluoroalkylsulfonyl)imides; and alkylammonium salts of organic acids such as triethylammonium salt of 10-camphorsulfonic acid. A variety of amine salts of aromatic (anthracene, naphthalene, or benzene derivative) sulfonic acids, including those disclosed in U.S. Pat. No. 3,474,054 (Patent Literature 4), U.S. Pat. No. 4,200,729 (Patent Literature 5), U.S. Pat. No. 4,251,665 (Patent Literature 6), and U.S. Pat. No. 5,187,019 (Patent Literature 7), can be used as the TAG.

The following are exemplified embodiments of the thermal acid generator that can be contained in the composition. The scope of the present invention is not limited to them.

[Formula xxxvii]

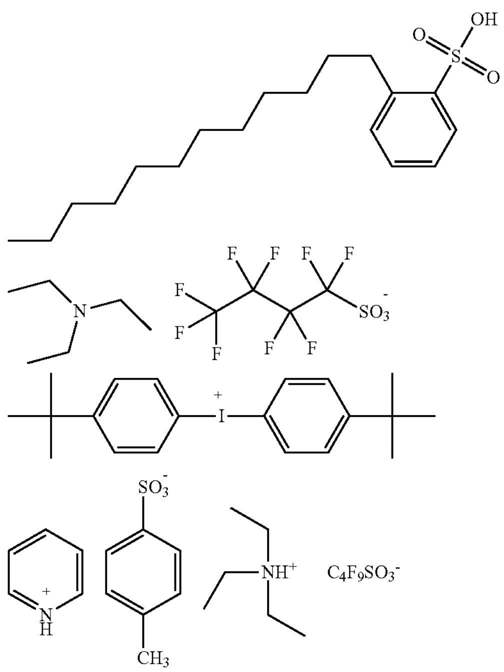

Given the ease of process control, the present invention may be implemented as an embodiment in which the acid generator is not added to the composition (this means that the amount of the acid generator is 0% by mass relative to the mass of the semiconductor material of formula (1)).

Radical Generator

A radical generator can be added to the composition to initiate polymerization. The radical generator generates radicals when heated, and examples thereof include azo compounds and peroxides. Exemplified embodiments of the radical generator include: organic peroxides, including hydroperoxides such as diisopropylbenzene hydroperoxide, cumene hydroperoxide, and t-butyl hydroperoxide, dialkyl peroxides such as $\alpha,\alpha$-bis(t-butylperoxy-m-isopropyl)benzene, dicumyl peroxide, 2,5-dimethyl-2,5-bis(t-butylperoxy)hexane, t-butyl cumyl peroxide, di-t-butyl peroxide, 2,5-dimethyl-2,5-bis(t-butylperoxy)hexyne-3, and t-butyl peroxy-2-ethylhexanoate, ketone peroxides, peroxyketals such as n-butyl 4,4-di(t-butylperoxy)valerate, diacyl peroxides, peroxydicarbonates, and peroxyesters; and azo compounds such as 2,2'-azobisisobutyronitrile, 1,1'-(cyclohexane-1-1-carbonitrile), 2,2'-azobis(2-cyclopropylpropionitrile), and 2,2'-azobis(2,4-dimethylvaleronitrile). These thermal radical generators may be used alone or in combination with one another and are preferably used alone. These known radical generators can be used in the composition, and these radical generators are available, for example, from NOF CORPORATION.

Given the ease of process control, the present invention may be implemented as an embodiment in which the radical generator is not added to the composition (this means that the amount of the radical generator is 0% by mass relative to the mass of the semiconductor material of formula (1)).

Other Components

To the composition according to the present invention there may be further added other components such as an agent for enhancing the adhesion to substrates, a lubricating agent, a monomeric dye, a lower alcohol ($C_{1-6}$ alcohol), a surface leveling agent, an anti-foaming agent, and a preservative agent. The amount of these components in the composition is preferably 0.1-10% by mass and more preferably 0.5-5% by mass relative to the amount of the semiconductor material of formula (I) in the composition. In an aspect of the present invention, the composition contains none (0% by mass) of these components.

Underlayer-Forming Composition

The composition according to the present invention is advantageous as an underlayer-forming composition used, for example, for producing a pattern by a lithography technique. The lithography technique employs various coatings (which may also be referred to as "layers") with different purposes to form a fine pattern. The composition is advantageously used to form such a coating due to its good coating formation property and gap filling property.

The underlayer is a coating formed between a substrate and a photoresist layer, and examples of the underlayer include a planarizing coating, an adhesive layer, and a bottom anti-reflective coating (BARC layer). The underlayer alone may have the functions of these layers or coatings; for example, the underlayer may function both as a planarizing coating and as a BARC layer. The underlayer-forming composition is a composition for forming an underlayer. A preferred embodiment of the underlayer is a planarizing coating, and a preferred embodiment of the underlayer-forming composition is a planarizing coating-forming composition.

The planarizing coating-forming composition according to the present invention is a composition that can be formed into a coating placed between a substrate and a photoresist coating and having an upper surface (the surface facing the photoresist) having high flatness. Preferably, an interlayer (such as a Si-containing resist interlayer, an adhesive layer, a bottom anti-reflective coating, or any combination of any of these) may be formed on the upper surface of the planarizing coating (the surface facing the photoresist), and the photoresist layer may be formed on the interlayer. The substrate used in the present invention may be a flat substrate, in view of high etching resistance of the composition and the ease of handling. Even when the substrate is a not-flat substrate, the composition of the present invention exhibits its effect sufficiently by virtue of having good gap filling property.

The planarizing coating can also be effectively used as a hard mask layer, since the semiconductor material has high heat resistance, high etching resistance, and advantageous filling property. Hard mask layers are formed to a large thickness (1,000-3,000 nm, for example); thus, the fact that a heat-induced decrease in thickness is small is advantageous in preventing distortion of the coatings. Additionally, hard mask layers are required to have higher etching resistance than common planarizing coatings and spin-on-carbon coatings (SOC coatings). A preferred embodiment of the planarizing coating-forming composition is a hard mask layer-forming composition.

Method for Manufacturing Planarizing Coating

An embodiment of the method for forming a planarizing coating according to the present invention will be described. The below-described method and conditions of coating formation are applicable to other coatings formed from the composition according to the present invention and to the underlayer according to the present invention.

As previously described, the "planarizing coating-forming composition" refers to a composition that can be formed into a coating placed between a substrate and a photoresist coating and having an upper surface (the surface facing the photoresist) having high flatness. Having high flatness means that the upper surface of the planarizing coating formed is horizontal. When the planarizing coating has high flatness, the variation in distance between the horizontally positioned bottom surface of a substrate (or the lowest substrate of plural stacked substrates) and the upper surface of the coating is small. A "flat substrate" refers to a substrate in which the distance between the bottom surface and top surface is substantially constant (the variation in the distance is from 0-3% in the substrate).

A "not-flat substrate" broadly refers to a substrate that is not a flat substrate. Examples of the non-flat substrate in the present invention include a stepped substrate and an concave-convex substrate. Exemplified embodiments of the non-flat substrate include a metal-containing substrate in which the height difference between the top part and the lower part of the substrate surface is 10-10,000 nm. The height difference is preferably 50-1,000 nm and more preferably 100-1,000 nm. Other examples of the non-flat substrate include a substrate having a wall or contact hole resulting from pre-treatment. The wall or contact hole can be formed by a known technique such as lithography, etching, or DSA, and preferably has an aspect ratio of 10-100 (preferably 25-75). Furthermore, the planarizing coating-forming composition according to the present invention is applicable to a substrate with a step. The height of the step is preferably 10-10,000 nm, more preferably 50-1,000 nm, and further preferably 100-1,000 nm.

When the planarizing coating-forming composition according to the present invention is applied to a flat substrate (bare wafer) and formed into a planarizing coating by heating, the planarizing coating can have a thickness of 20-3,000 nm (preferably 100-2,000 nm, more preferably 200-400 nm).

The substrate used can be a flat substrate or non-flat substrate as described above.

The substrate used can be a metal-containing substrate or a silicon-containing substrate. The substrate used in the present invention may be a single-layer substrate or a multi-layer substrate composed of plural substrate layers. As the substrate there can be used any known substrate such as a silicon-coated substrate, silicon dioxide-coated substrate, silicon nitride-coated substrate, silicon wafer substrate (such as a $SiO_2$ wafer), glass substrate, indium-containing substrate (such as an ITO substrate), or titanium-containing substrate (such as a titanium nitride or titanium oxide substrate).

In the process for manufacturing a semiconductor according to the present invention, any known manner can be employed for the configuration of the substrate according to the conditions of the process. Examples of the configuration of the substrate include the multi-layer configurations listed below. The left-to-right direction in the following list corresponds to the bottom-to-top direction in the multi-layer configurations.

Silicon wafer substrate

Silicon wafer substrate/titanium-containing substrate

Silicon wafer substrate/titanium-containing substrate/silicon-coated substrate

Silicon wafer substrate/titanium-containing substrate/silicon dioxide-coated substrate Silicon wafer substrate/silicon dioxide-coated substrate/titanium-containing substrate Silicon nitride substrate Silicon nitride substrate/titanium-containing substrate Silicon nitride substrate/titanium-containing substrate/silicon-coated substrate Silicon nitride substrate/titanium-containing substrate/silicon dioxide-coated substrate Silicon nitride substrate/silicon dioxide-coated substrate/titanium-containing substrate One substrate to be laminated on another substrate can be formed by a known technique such as CVD. The one substrate can be patterned by a known lithography technique or etching technique. Still another substrate can be laminated on the patterned substrate by a known technique such as CVD.

In the present invention, a layer of the composition is formed above a substrate. The layer formation can be accomplished by a known method, and a preferred method is application. The application can be carried out by known means such as a spinner or coater. In the application of the composition to the substrate, it is preferable for the substrate and the composition to come into direct contact with each other, although the composition may be applied with another thin coating (such as a substrate-modifying layer) interposed between the composition and the substrate. The applied composition is then heated to form a coating. As for the heating conditions, the heating temperature is typically selected from the range of 150-650° C. (preferably 200-650° C., more preferably 250-600° C.), and the heating time is typically selected from the range of 30-180 seconds (preferably 30-120 seconds). Even when the heating is carried out at 400-500° C. for 0.5-8 hours, the decrease in coating thickness is small because of the high heat resistance of the semiconductor material. The heating can be carried out in separate steps (multi-step bake). For example, the heating may be two-step heating consisting of: first heating by which the substrate is gap-filled along with removal of the solvent; and second heating by which the composition is mildly reflowed and thus formed into a coating with high flatness. For example, it is preferable that the first heating be performed at 200-300° C. for 30-120 seconds and the second heating be performed at 300-650° C. for 30-120 seconds. The heating may be performed in an air atmosphere, whose oxygen concentration can be reduced to prevent oxidation of the planarizing coating composition and planarizing coating. For example, the oxygen concentration may be adjusted to 1,000 ppm or less (preferably 100 ppm or less) by introducing an inert gas ($N_2$, Ar, He, or any mixture of any of these) into the atmosphere.

The coating is suitable as a planarizing coating to be formed by spin-on coating, since the coating has a high carbon content and hence a low etching rate due to containing the semiconductor material of formula (1). The evaluation of the etching rate can be made by a known technique. For example, the ratio of the etching rate of the coating to that of a resist (UV 1610, manufactured by Dow Chemical Company) is preferably 1.0 or less, more preferably 0.9 or less, and further preferably 0.8 or less.

In an example, the coating formation is accomplished by formation of a solid component into a layer after removal of the solvent. In another example, the coating formation is accomplished by bonding of plural solid components to each other. The phrase "bonding of plural solid components" is intended to include not only the case where the molecules of all of the solid components in the composition are bonded to each other, but also the case where the molecules of some of the solid components in the composition are bonded to each other.

Formation of Photoresist Coating and Other Coatings

A photoresist composition (such as a positive-type photoresist composition) is applied to the coating formed as described above. The coating formed from the composition according to the present invention above the substrate and below the photoresist coating is an underlayer. The positive-type photoresist composition refers to a photoresist composition that undergoes a reaction under light irradiation and whose light-irradiated portion has an increased solubility in a developer. The photoresist composition used is not particularly limited, and any positive-type photoresist composition, negative-type photoresist composition, or negative tone development (NTD) photoresist composition can be used, as long as the photoresist composition is sensitive to the exposure light for pattern formation.

In the method for manufacturing a resist pattern according to the present invention, a coating or layer other than the underlayer formed from the composition according to the present invention and the photoresist coating may be present. An interlayer may be interposed between the underlayer and the photoresist coating so that the underlayer and the photoresist coating are not in direct contact with each other. The interlayer is a coating formed between the photoresist coating and the underlayer, and examples of the interlayer include a bottom anti-reflecting coating (BARC layer), an inorganic hard mask interlayer (such as a silicon oxide coating, silicon nitride coating, or silicon oxynitride coating), and an adhesive coating. The inorganic hard mask interlayer can be formed by reference to Japanese Patent No. 5336306 B2 (Patent Literature 8). The interlayer may consist of a single layer or plural layers. A top anti-reflective coating (TARC layer) may be formed above the photoresist coating.

In the process for manufacturing a semiconductor according to the present invention, any known manner can be employed for the configuration of the layers other than the underlayer according to the conditions of the process. Examples include the following multi-layer configurations.

Substrate/underlayer/photoresist coating

Substrate/planarizing coating/BARC layer/photoresist coating

Substrate/planarizing coating/BARC layer/photoresist coating/TARC layer

Substrate/planarizing coating/inorganic hard mask interlayer/photoresist coating/TARC layer Substrate/planarizing coating/inorganic hard mask interlayer/BARC layer/photoresist coating/TARC layer Substrate/planarizing coating/adhesive coating/BARC layer/photoresist coating/TARC layer Substrate/substrate-modifying layer/planarizing coating/BARC layer/photoresist coating/TARC layer Substrate/substrate-modifying layer/planarizing coating/adhesive coating/BARC layer/photoresist coating/TARC layer These layers can be cured by heating and/or exposure after being applied or can be formed by a known technique such as CVD. These layers can be removed by a known technique (such as etching) and can each be patterned through an upper layer as a mask.

The coating formed from the composition according to the present invention is preferably an underlayer, more preferably a planarizing coating or a BARC layer, and further preferably a planarizing coating. The coating formed from the composition according to the present invention is not suitable as an inorganic hard interlayer.

In an aspect of the present invention, the underlayer can be formed on a non-flat substrate, and another substrate can be formed on the underlayer. The other substrate can be formed, for example, by a technique such as CVD. The lower substrate and the upper substrate may have the same composition or different compositions. Still another layer can further be formed on the upper substrate. Forming the bottom coating or a photoresist coating as the other layer enables processing of the upper substrate. A photoresist coating or another coating that can be employed is as described above.

Patterning and Device Manufacturing

The photoresist coating is exposed through a given mask. The wavelength of the light used for exposure is not particularly limited. The exposure is preferably performed with light having a wavelength of 13.5-248 nm. In particular, KrF excimer laser (wavelength: 248 nm), ArF excimer laser (wavelength: 193 nm), or extreme ultraviolet light (wavelength: 13.5 nm) can be used, and KrF excimer laser is more preferred. These wavelengths may vary within ±1%. The exposure can, if desired, be followed by post-exposure bake. The temperature for the post-exposure bake is selected from the range of 80-150° C., preferably 100-140° C., and the heating time for the post-exposure bake is selected from the range of 0.3-5 minutes, preferably 0.5-2 minutes.

Next, development is performed with a developer. When a positive-type photoresist composition is used, the exposed part of the positive-type photoresist layer is removed by the development, resulting in the formation of a photoresist pattern. This photoresist pattern can be made finer using, for example, a shrink material.

A 2.38% by mass aqueous TMAH solution is preferred as the developer used for the development in the above photoresist pattern formation method. The use of such a developer allows easy dissolution and removal of the planarizing coating at room temperature. An additive such as a surfactant can be added to the developer. The temperature of the developer is typically selected from the range of 5-50° C., preferably 25-40° C., and the development time is typically selected from the range of 10-300 seconds, preferably 30-60 seconds.

The interlayer, underlayer, and/or substrate can be patterned through the resulting photoresist pattern as a mask. For the pattern formation, a known technique such as etching (dry etching or wet etching) can be used. For example, the interlayer may be etched through the photoresist pattern as an etching mask, and then the planarizing coating and substrate may be etched through the resulting interlayer pattern as an etching mask to form a pattern on the substrate. Alternatively, the inorganic hard mask interlayer may be etched through the photoresist pattern as an etching mask, the planarizing coating may be etched through the resulting inorganic hard mask interlayer pattern as an etching mask, and then the substrate may be etched through the resulting planarizing coating pattern as an etching mask to form a pattern on the substrate. Alternatively, a layer below the photoresist layer (such as an interlayer and/or underlayer) may be etched through the photoresist pattern as an etching mask and, at the same time, the substrate may be etched through the photoresist pattern as an etching mask. Wiring can be formed in the substrate using the pattern formed on the substrate.

For example, the underlayer can be suitably removed by dry etching with $O_2$, $CF_4$, $CHF_3$, $Cl_2$, or $BCl_3$. $O_2$ or $CF_4$ can be suitably used.

Subsequently, the substrate, if necessary, is further processed to form a device. Such further processing can be done by using a known method. After formation of the device, the substrate, if necessary, is cut into chips, which are connected to a leadframe and packaged with a resin. In the present invention, the packaged product is referred to as a semiconductor.

Novel Compound and Method for Synthesizing the Same

The present invention provides a novel compound represented by formula (9)'.

[Formula xii]

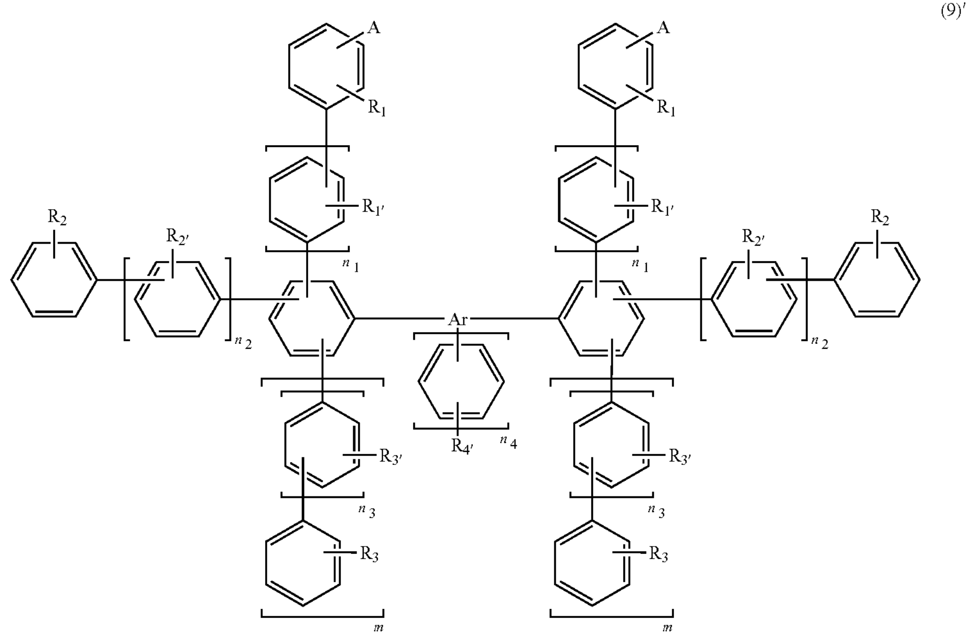

wherein

A is —OH, —$NH_2$, or —SH, $R_1$ is hydrogen, —OH, —$NH_2$, —SH, linear $C_{1-10}$ alkyl, branched $C_{3-10}$ alkyl, or a direct bond to a phenyl ring, $R_{1'}$ is hydrogen, —OH, —$NH_2$, —SH, linear $C_{1-10}$ alkyl, branched $C_{3-10}$ alkyl, or a direct bond to a phenyl ring, $R_2$ is hydrogen, —OH, —$NH_2$, —SH, linear $C_{1-10}$ alkyl, branched $C_{3-10}$ alkyl, or a direct bond to a phenyl ring, $R_{2'}$ is hydrogen, —OH, —$NH_2$, —SH, linear $C_{1-10}$ alkyl, branched $C_{3-10}$ alkyl, or a direct bond to a phenyl ring, $R_3$ is hydrogen, —OH, —$NH_2$, —SH, linear $C_{1-10}$ alkyl, branched $C_{3-10}$ alkyl, or a direct bond to a phenyl ring, $R_{3'}$ is hydrogen, —OH, —$NH_2$, —SH, linear $C_{1-10}$ alkyl, branched $C_{3-10}$ alkyl, or a direct bond to a phenyl ring, $n_1$ is 0, 1, or 2, $n_2$ is 0, 1, or 2, $n_3$ is 0, 1, or 2, m is 0, 1, 2, or 3, Ar is a $C_{6-20}$ aromatic hydrocarbon ring, $R_{4'}$ is hydrogen, —OH, —$NH_2$, —SH, linear $C_{1-10}$ alkyl, branched $C_{3-10}$ alkyl, or a direct bond to a phenyl ring, and $n_4$ is 0, 1, 2, 3, or 4, provided that the following compounds are excluded from Formula (9)':

[Formula xiii]

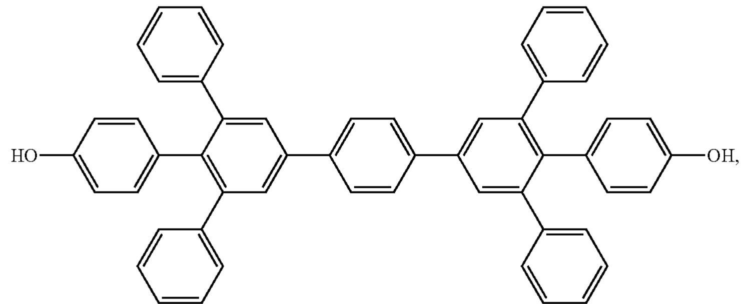

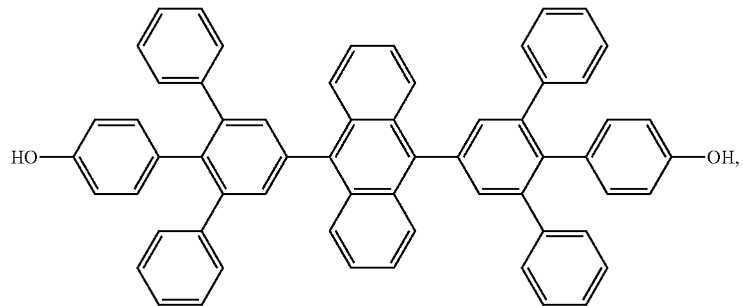

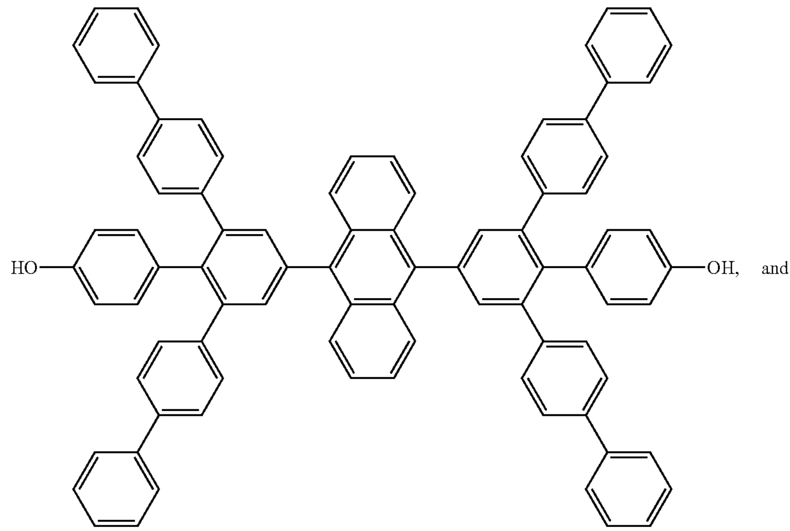

-continued

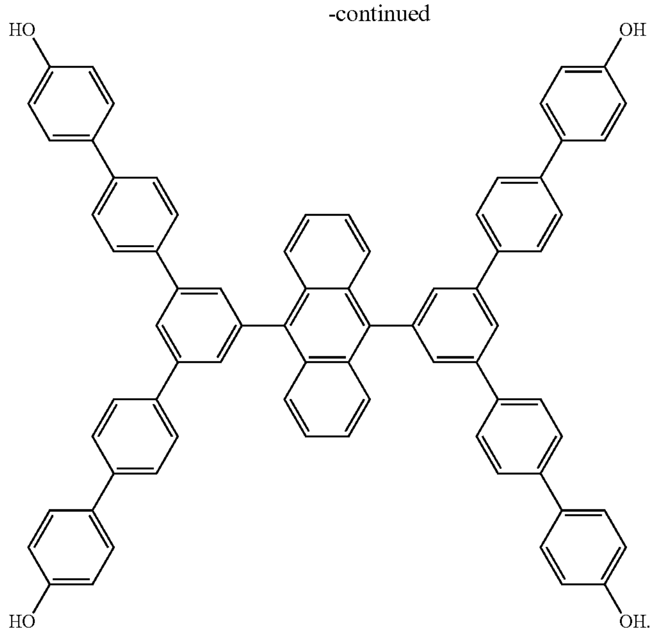

Compounds of formula (9)', excluding the compounds shown in [Formula xiii], are identical to compounds of formula (9) for semiconductor materials. Preferred examples of the compounds of formula (9)' are also the same as those mentioned above for formula (9). Formula (15) and formula (16) are species concepts of formula (9); thus, preferred examples of the compounds of formula (9)' include compounds of formula (15) and formula (16) for semiconductor materials, except for the excluded compounds shown in [Formula xiii].

A compound represented by formula (9)' is not a precursor produced as an intermediate on the synthesis route, but can be used itself. For example, the compound can be used in a lithography process in semiconductor manufacturing.

Compounds represented by formula (9)' can be produced in the same manner as compounds of formula (9) for semiconductor materials.

EXAMPLES

Hereinafter, the present invention will be described with working examples. These examples are given only for illustrative purpose and not intended to limit the scope of the present invention. The term "part(s)" as used in the following description refers to part(s) by mass, unless otherwise stated.

Synthesis Example 1 of G1

A reaction vessel equipped with a stirrer, a condenser (Liebig condenser), a heater, a nitrogen inlet tube, and a temperature controller was prepared. The reaction vessel was charged with 3,4-bis(4-methoxyphenyl)-2,5-diphenylcyclopenta-2,4-dienone (140 parts), 1,4-bis(phenylethynyl) benzene (42 parts, Wako Pure Chemical Industries, Ltd.), and diphenyl ether (546 parts), which were stirred in a nitrogen atmosphere at 250° C. for 48 hours to allow the reaction to proceed. The 3,4-bis(4-methoxyphenyl)-2,5-diphenylcyclopenta-2,4-dienone was synthesized beforehand according to Synthetic Metals vol. 200, p 85-Zheng Bang Lim et al, (2015). After completion of the reaction, the reaction solution was cooled to normal temperature. This reaction solution was poured into stirred methanol (1900 parts) to give a precipitate, and the precipitate was separated by filtration through filter paper with a pore size of 1 μm. The precipitate was dried under vacuum at 150° C. to obtain 155 parts of an intermediate G0 (yield: 93%).

[Formula xxxviii]

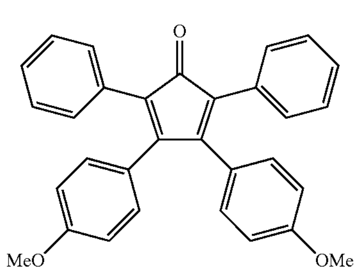

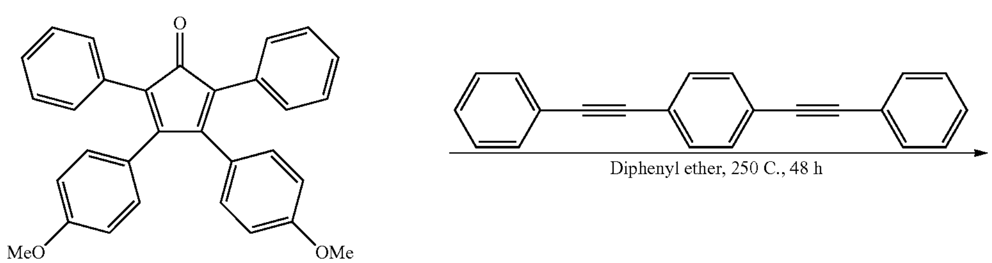

-continued

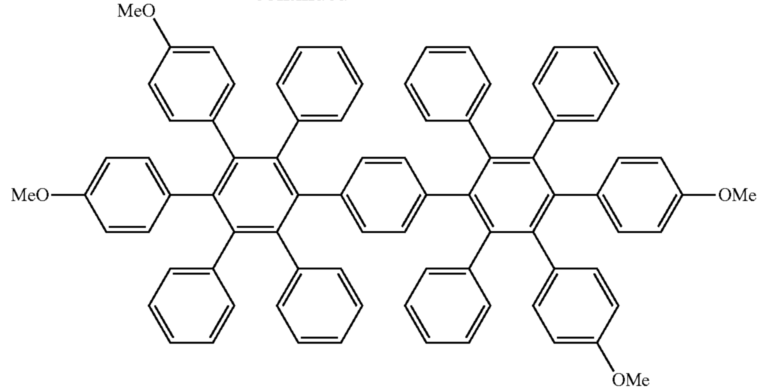

The G0 thus obtained was transferred to another reaction vessel, to which a stirrer, a nitrogen inlet tube, and a temperature controller were attached. The reaction vessel was charged with the intermediate G0 (100 parts) and dichloromethane (941 parts), and the reaction temperature was maintained at −40° C. in a nitrogen atmosphere. After that, 372 parts of a dichloromethane solution of boron tribromide (1 mol/L) was slowly added dropwise. After the dropwise addition, the temperature of the reaction vessel was slowly cooled to room temperature (25° C.), and then the contents of the reaction vessel were stirred at room temperature for 12 hours to allow the reaction to proceed. Water (1,000 parts) was then slowly added to the stirred reaction solution to terminate the reaction. After that, dichloromethane in the reaction product was distilled off under reduced pressure at 80° C. to give a precipitate. The precipitate was subjected to ethyl acetate washing by dissolving it in an adequate amount of stirred ethyl acetate (4,000 parts). Ethyl acetate was distilled off under reduced pressure, and the resulting precipitate was dried under vacuum at 1500° C. to obtain 92 parts of G1 (total yield: 90%, yield of G1 from G0: 97%).

[Formula xxxix]

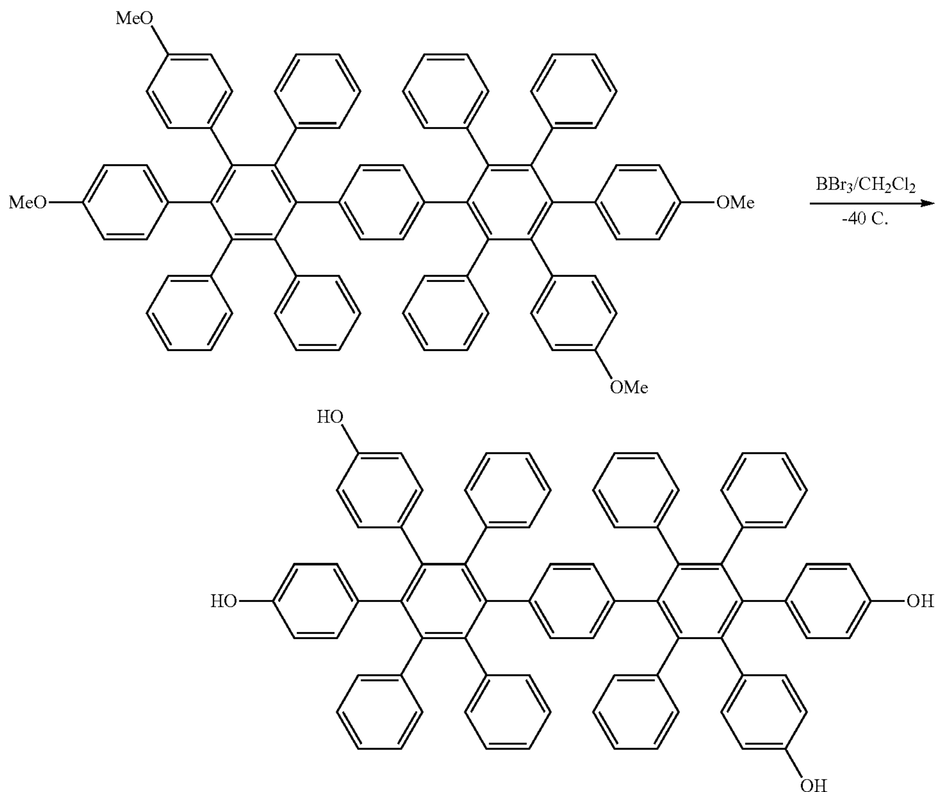

The following is the result of NMR spectroscopy of G1, and this result confirms that G1 has the above structure.

$^{1}$H-NMR (400 MHz in $CDCl_3$ (1)/$CF_3COOD$ (1)): 6.98-6.70 (m, 40H, Ph), 6.43 (m, 10H, Ph)

$^{13}$C-NMR (100 MHz in $CDCl_3$ (1)/$CF_3COOD$ (1)): 157.4, 134.3, 133.6, 132.5, 130.5, 129.2, 127.9, 127.6, 127.2, 126.2, 116.4.

Synthesis Example 2 of G2

Synthesis was carried out in the same manner as in Synthesis Example 1, except for replacing 1,4-bis(phenylethynyl)benzene with 9,10-bis(phenylethynyl)anthracene. The total yield was 75%.

[Formula xI]

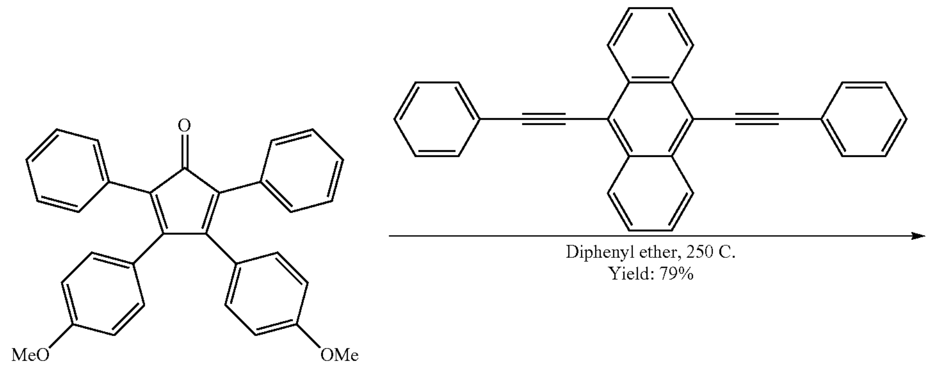

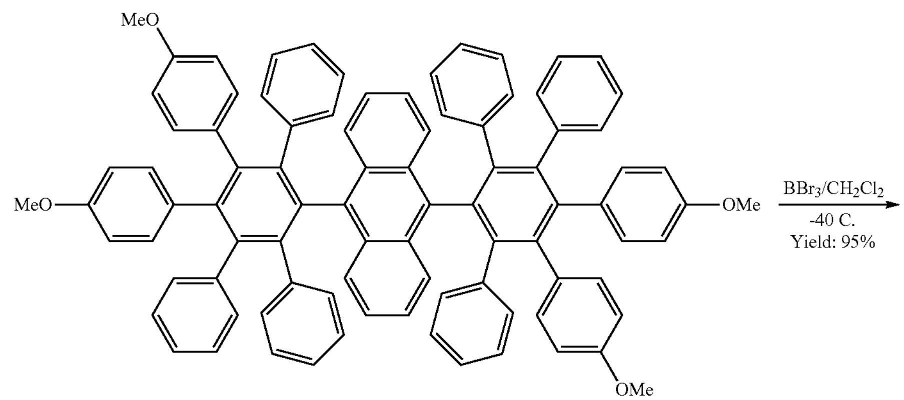

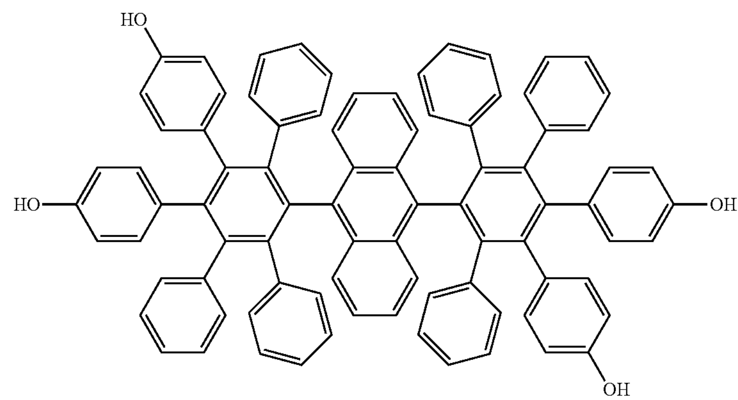

G2

The following is the result of NMR spectroscopy of G2, and this result confirms that G2 has the above structure.

$^{1}$H-NMR (400 MHz in $CDCl_3$ (1)/$CF_3OOD$ (1)): 7.91-7.39 (m, 46H, Ph), 6.43 (m, 8H, Ph)

$^{13}$C-NMR (100 MHz in $CDCl_3$ (1)/$CF_3OOD$ (1)): 157.4, 134.3, 133.6, 133.1, 130.9, 130.5, 129.2, 127.9, 127.6, 126.2, 126.1, 125.6, 116.4

Synthesis Example 3 of G3

Synthesis was carried out in the same manner as in Synthesis Example 1, except for replacing 1,4-bis(phenylethynyl)benzene with 1,4-diethynylbenzene. The total yield was 85%.

[Formula xli]

G3

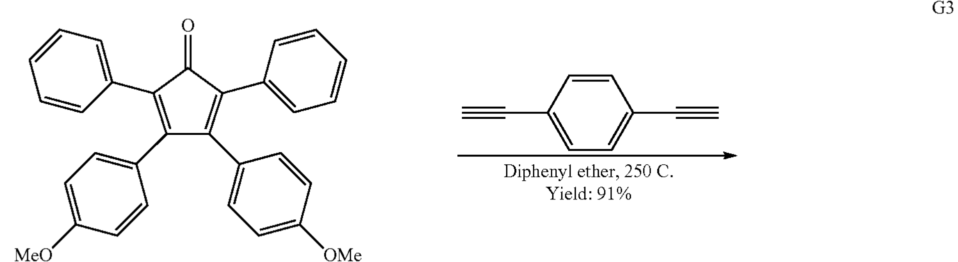

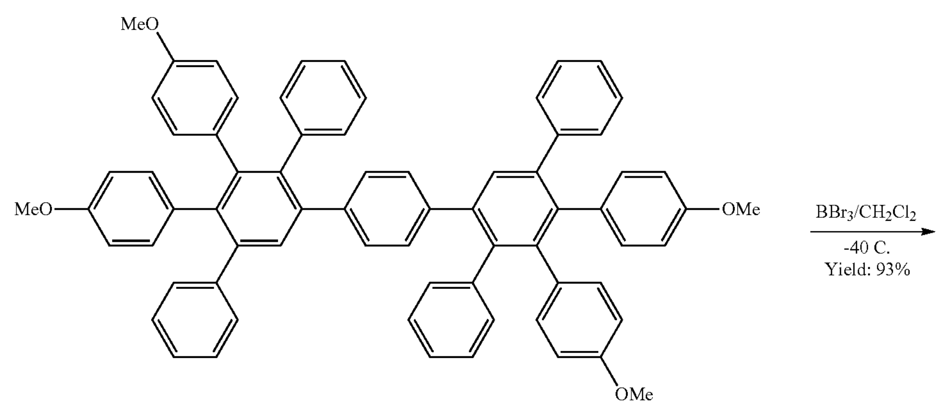

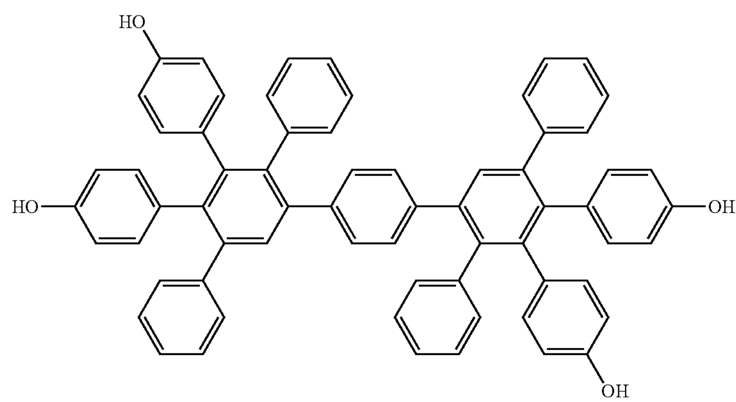

The following is the result of NMR spectroscopy of G3, and this result confirms that G3 has the above structure.

$^{1}$H-NMR (400 MHz in $CDCl_3$ (1)/$CF_3COOD$ (1)): 7.79-7.25 (m, 34H, Ph), 6.86 (m, 8H, Ph)

$^{13}$C-NMR (100 MHz in $CDCl_3$ (1)/$CF_3COOD$ (1)): 157.4, 142.0, 140.9, 135.4, 133.8, 133.6, 130.5, 129.2, 127.9, 127.6, 127.2, 126.2, 126.1, 116.4.

Synthesis Example 4 of G4

Synthesis was carried out in the same manner as in Synthesis Example 1, except for replacing 3,4-bis(4-methoxyphenyl)-2,5-diphenylcyclopenta-2,4-dienone with 1,3-di(phenyl)-2H-cyclopenta[1]phenanthren-2-one and replacing 1,4-bis(phenylethynyl)benzene with 1,4-bis((4-methoxyphenyl)ethynyl)benzene. The total yield was 79%.

[Formula xlii)

G4

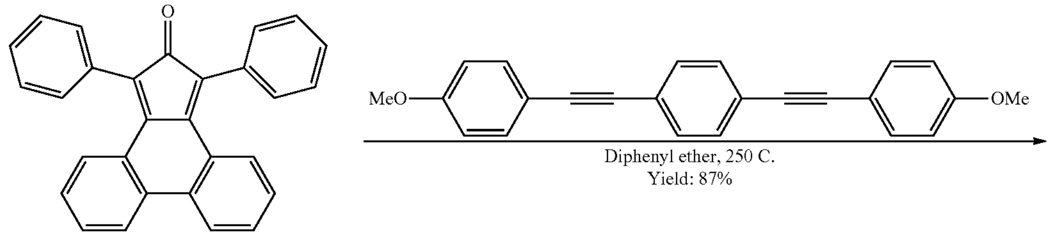

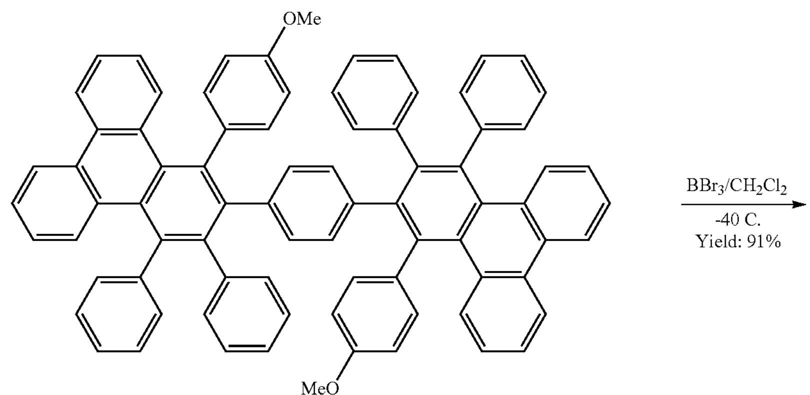

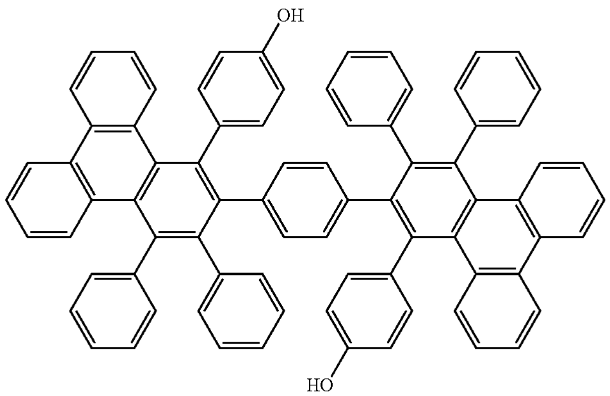

The following is the result of NMR spectroscopy of G4, and this result confirms that G4 has the above structure.

$^{1}$H-NMR (400 MHz in $CDCl_3$ (1)/$CF_3COOD$ (1)): 8.93 (m, 4H, Ph), 8.12-7.25 (m, 40H, Ph), 6.86 (m, 4H, Ph)

$^{13}$C-NMR (100 MHz in $CDCl_3$ (1)/$CF_3COOD$ (1)): 157.4, 133.6, 132.5, 130.5, 129.6, 129.2, 128.3, 127.9, 127.6, 127.2, 126.6, 126.2, 126.1, 124.6, 123.9, 122.6, 122.5, 122.1, 120.8, 118.7, 116.4.

Synthesis Example 5 of G5

Synthesis was carried out in the same manner as in Synthesis Example 1, except for replacing 3,4-bis(4-methoxyphenyl)-2,5-diphenylcyclopenta-2,4-dienone with 2,3,4,5-tetrakis(4-methoxyphenyl)cyclopenta-2,4-dienone and replacing 1,4-bis(phenylethynyl)benzene with 1,2-bis(4-methoxyphenyl)ethyne. The total yield was 80%.

[Formula xliii]

G5

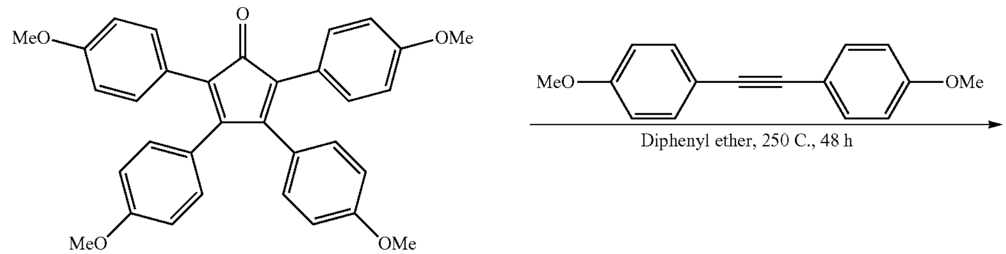

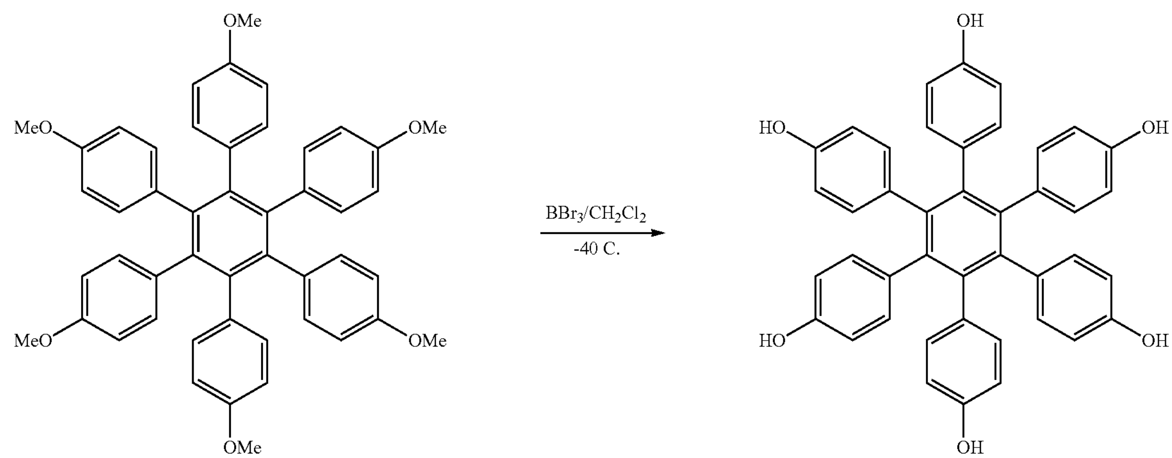

The following is the result of NMR spectroscopy of G5, and this result confirms that G5 has the above structure.

$^{1}$H-NMR (400 MHz in $CDCl_3$): 7.62 (m, 12H, Ph), 6.86 (m, 12H, Ph), 5.35 (m, 6H, OH).

$^{13}$C-NMR (100 MHz in $CDCl_3$): 157.4, 134.3, 130.5, 126.2, 116.4.

Synthesis Example 6 of G6

Synthesis was carried out in the same manner as in Synthesis Example 1, except for replacing 1,4-bis(phenylethynyl)benzene with 4,4'-bis(phenylethynyl)-1,1'-biphenyl. The total yield was 75%.

[Formula xliv]

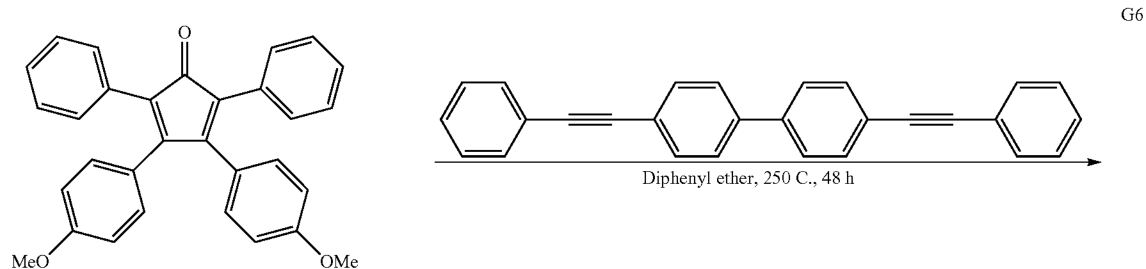

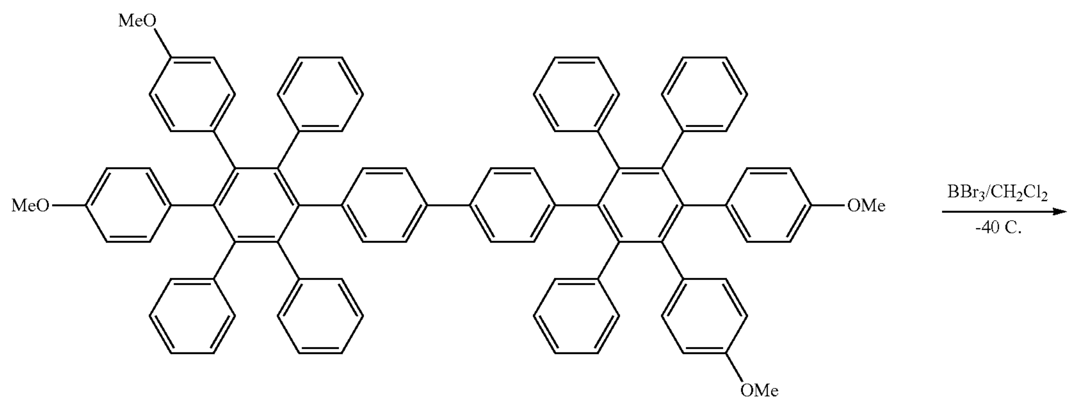

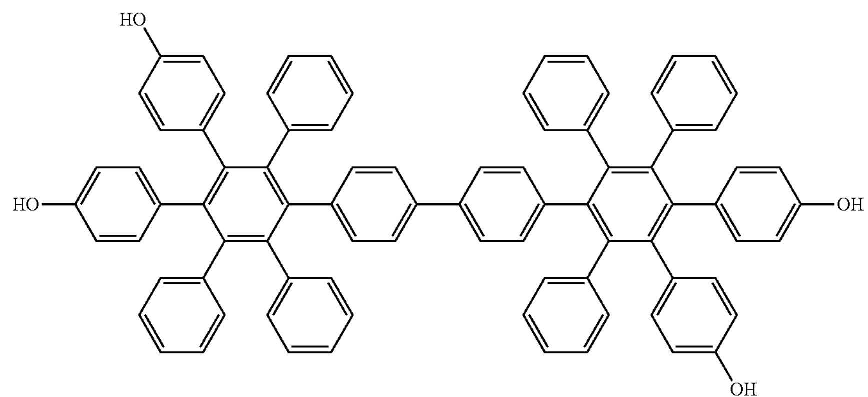

The following is the result of NMR spectroscopy of G6, and this result confirms that G6 has the above structure.

$^{1}$H-NMR (400 MHz in $CDCl_3$ (1)/$CF_3COOD$ (1)): 7.62 (m, 8H, Ph), 7.52-7.51 (m, 24H, Ph), 7.41 (m, 6H, Ph), 7.25 (m, 8H, Ph), 6.86 (m, 8H, Ph).

$^{13}$C-NMR (100 MHz in $CDCl_3$ (1)/$CF_3COOD$ (1)): 157.4, 139.7, 134.3, 133.6, 132.5, 130.5, 129.2, 127.9, 127.6, 127.2, 126.2, 116.4.

Synthesis Example 7 of G7

Synthesis was carried out in the same manner as in Synthesis Example 1, except for replacing 1,4-bis(phenylethynyl)benzene with 5'-phenyl-2',4',6'-tris(phenylethynyl)-1,1',3',1"-ter-phenyl. The total yield was 64%.

[Formula xiv]

G7

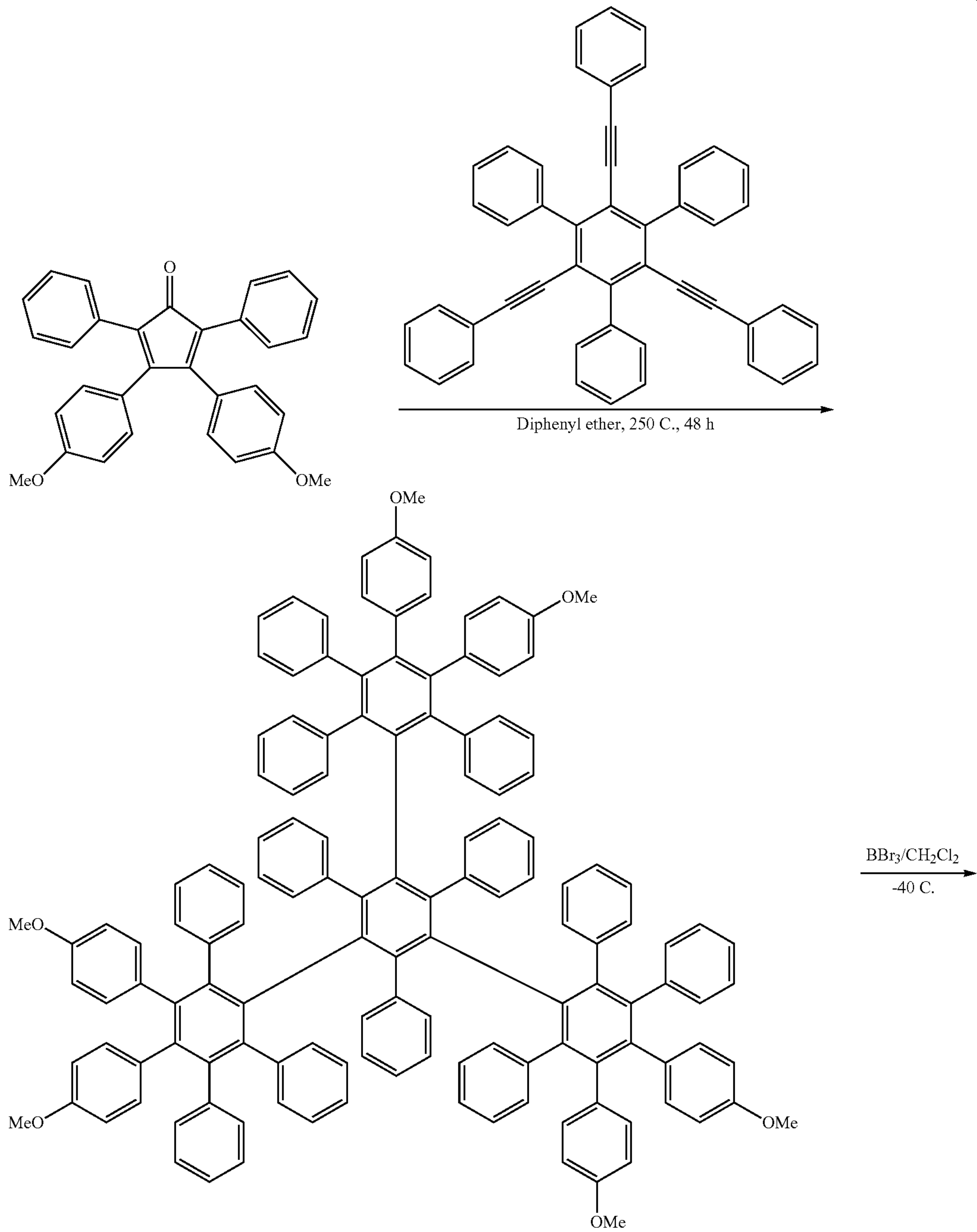

$BBr_3/CH_2Cl_2$

-40 C.

-continued

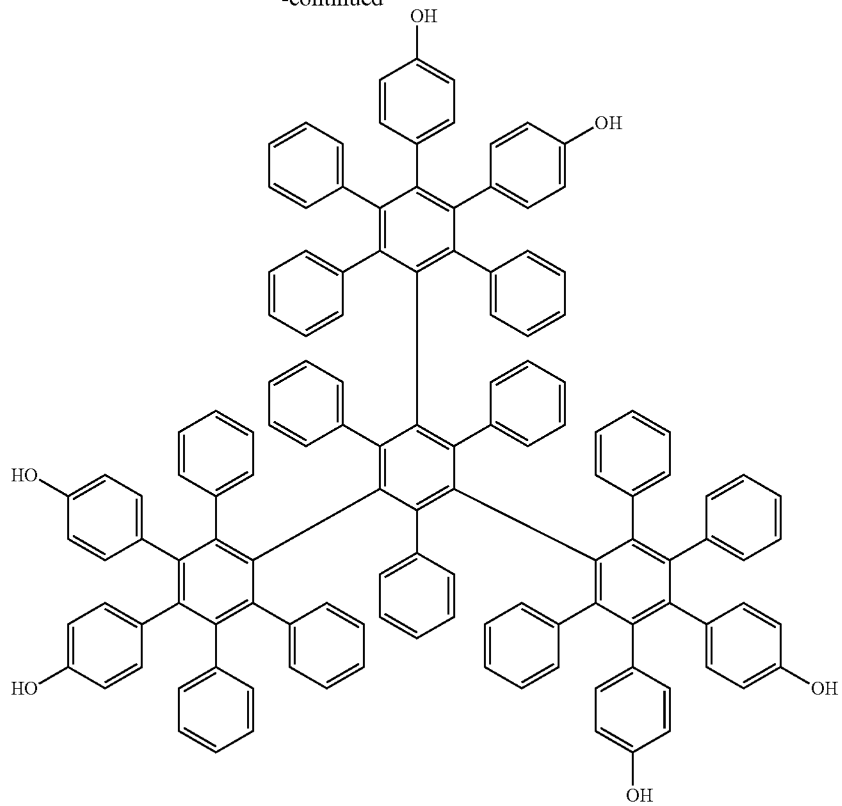 [SMILES: Oc1ccc(-c2c(-c3ccccc3)c(-c3ccccc3)c(-c3c(-c4ccccc4)c(-c4c(-c5ccccc5)c(-c5ccccc5)c(-c5ccc(O)cc5)c(-c5ccc(O)cc5)c4-c4ccccc4)c(-c4ccccc4)c(-c4c(-c5ccccc5)c(-c5ccccc5)c(-c5ccc(O)cc5)c(-c5ccc(O)cc5)c4-c4ccccc4)c3-c3ccccc3)c(-c3ccccc3)c2-c2ccc(O)cc2)cc1]

The following is the result of NMR spectroscopy of G7, and this result confirms that G7 has the above structure.

$^{1}$H-NMR (400 MHz in $CDCl_3$ (1)/$CF_3COOD$ (1)): 7.62 (m, 12H, Ph), 7.52-7.51 (m, 48H, Ph), 7.41 (m, 12H, Ph), 6.86 (m, 12H).

$^{13}$C-NMR (100 MHz in $CDCl_3$ (1)/$CF_3COOD$ (1)): 157.4, 134.3, 133.6, 130.5, 129.2, 127.9, 127.6, 126.2, 116.4.

Synthesis Example 8 of G8

Synthesis was carried out in the same manner as in Synthesis Example 1, except for replacing 3,4-bis(4-methoxyphenyl)-2,5-diphenylcyclopenta-2,4-dienone with 2,3,4,5-tetraphenylcyclopenta-2,4-dienone and replacing 1,4-bis(phenylethynyl)benzene with 4,4'-(ethyne-1,2-diyl)dianiline. The total yield was 58%.

[Formula xlvi]

G8

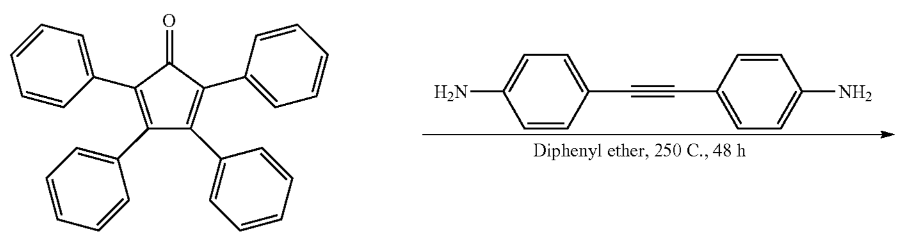

-continued

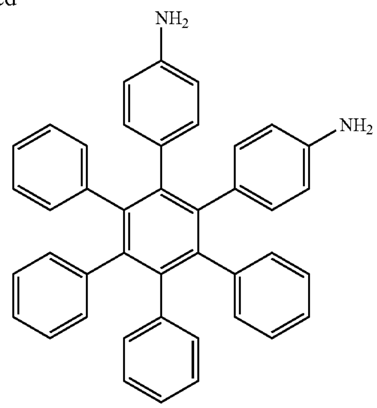

The following is the result of NMR spectroscopy of G8, and this result confirms that G8 has the above structure.

$^{1}$H-NMR (400 MHz in $CDCl_3$): 7.54 (m, 4H, Ph), 7.52-7.51 (m, 16H, Ph), 7.41 (m, 4H, Ph) 6.58 (m, 4H, Ph), 6.27 (br, 4H, $NH_2$).

$^{13}$C-NMR (100 MHz in $CDCl_3$): 144.5, 134.3, 133.6, 129.2, 128.7, 127.9, 127.6, 123.6, 119.8.

Comparative Example 1-1: Evaluation of Solubility of Comparative Compound 1

To evaluate the solubility of comparative compound 1 described in Angew. Chem. Int. Ed. Engl. 36 (No. 15), p 1607-(1997), the following experiment was conducted.

Comparative compound 1 was added as a solute to each of the various solvents listed in Table 1 in an amount of 10% by mass, and mixed with the solvent by stirring at room temperature for 60 minutes. When 10% by mass of the solute was not fully dissolved in the solvent, the amount of the solute added was changed to 1% by mass, and 1% by mass of the solute was mixed with the solvent in the same manner as above.

[Formula xlvii]

Comparative compound 1

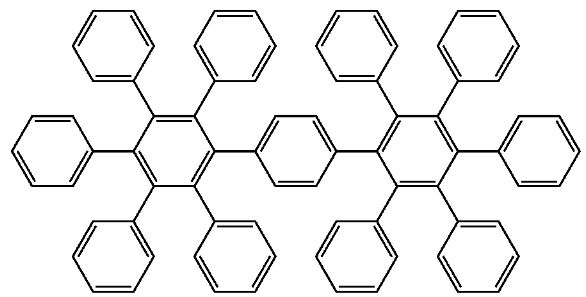

The state of dissolution of the solute was visually inspected and evaluated as follows.

A: Even when the amount of the solute mixed with the solvent was 10% by mass, the solute was fully dissolved.

B: When the amount of the solute mixed with the solvent was 10% by mass, the solute was not fully dissolved and some of it remained undissolved, while when the amount of the solute mixed with the solvent was 1% by mass, the solute was fully dissolved.

C: Even when the amount of the solute mixed with the solvent was 1% by mass, the solute was not fully dissolved and some of it remained undissolved.

TABLE 1

| | | Solvent | | |
|---|---|---|---|---|
| | Solute | PGME | PGME:PGMEA = 7:3 | PGME:EL = 7:3 |
| Example 1-1 | G1 | A | A | A |
| Example 1-2 | G2 | A | A | A |
| Example 1-3 | G3 | A | A | A |
| Example 1-4 | G4 | A | A | A |
| Example 1-5 | G5 | A | A | A |
| Example 1-6 | G6 | A | A | A |
| Example 1-7 | G7 | A | B | B |
| Example 1-8 | G8 | A | A | A |
| Comparative Example 1-1 | Comparative compound 1 | C | C | C |
| Reference Example 1-1 | Intermediate G0 | C | C | C |

The abbreviations used in the above table represent the compounds listed below. The expression “7:3” represents a liquid mixture in a volume ratio of 7:3. The same applies hereinafter.

PGME: Propylene glycol monomethyl ether

PGMEA: Propylene glycol 1-monomethyl ether 2-acetate

EL: Ethyl lactate

The compound according to the present invention has been proved to have high solubility in solvents.

Examples 1-1 to 1-4 and Reference Example 1-1: Evaluation of Solubility of Compound According to the Present Invention and Intermediate G0

Experiments were conducted in the same manner as above, except for changing the solute from comparative compound 1 to other compounds listed in Table 1. The evaluation results are shown in Table 1.

Preparation Example 1 of Composition 1

The composition listed in Table 1 was fully dissolved in a mixed solvent of PGME and PGMEA (PGME:PGMEA=7:3). The amount of the compound added was as shown in parts by mass in Table 1. The resulting solution was filtered through a 0.2 μm filter made of fluorine resin (SLFG025NS, manufactured by Merck Millipore) to obtain composition 1.

Preparation Examples 2 to 11 of Compositions 2 to 11 and Comparative Preparation Examples 1 to 3 of Comparative Compositions 1 to 3

Compositions 2 to 11 and comparative compositions 1 to 3 were obtained in the same manner as in Preparation Example 1, except for replacing the compound used in Preparation Example 1 with compounds listed in Table 1, crosslinking agents, and a thermal acid generator.

[Formula xlviii]

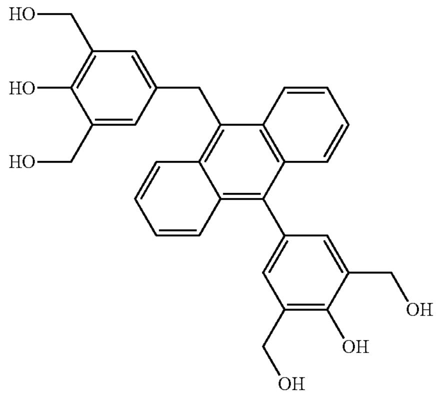

Crosslinking agent 1 (manufactured by Asahi Yukizai Corporation)

[Formula xlix]

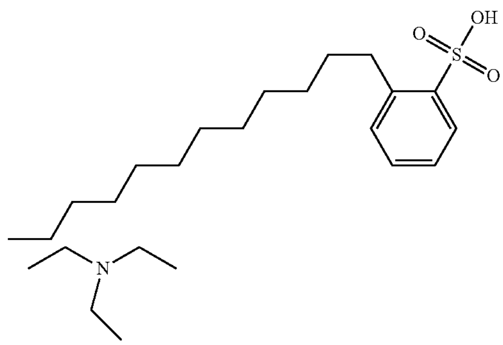

Thermal acid generator 1

Thermal acid generator 1 used was a mixture of the two compounds shown on the left (compound on the left:compound on the right=20:21 in a molar ratio). Both of the two compounds are manufactured by Tokyo Chemical Industry Co., Ltd.

[Formula I]

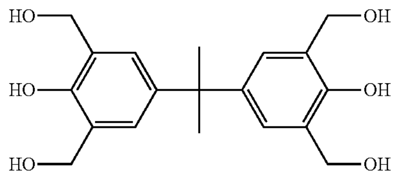

Crosslinking agent 2 (manufactured by Asahi Yukizai Corporation)

[Formula Ii]

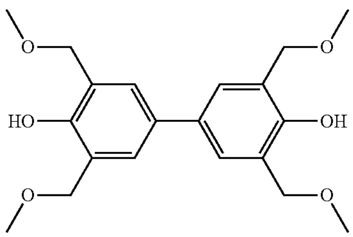

Crosslinking agent 3 (manufactured by Honshu Chemical Industry Co., Ltd.)

[Formula Iii]

Comparative polymer 2

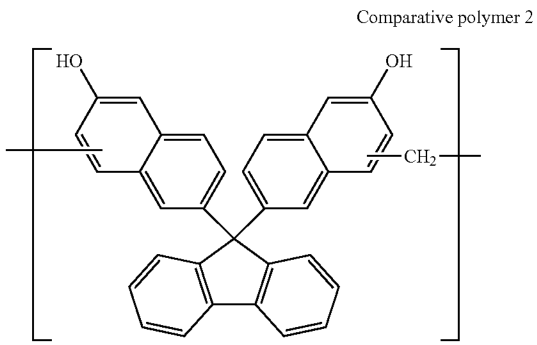

This polymer is described in Patent Literature 2. Mw=3,500, Mw/Mn=4.50

[Formula Iiii]

Comparative compound 3

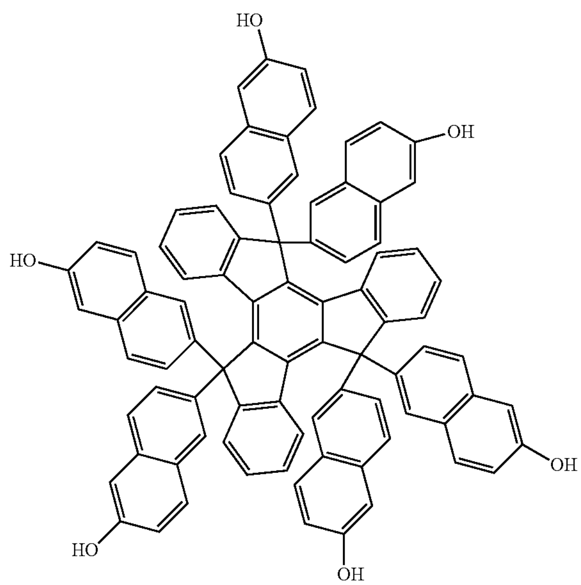

Examples 2-1 to 2-11 and Comparative Examples 2-1 to 2-3: Evaluation of Filling Property Each of compositions 1 to 11 and comparative compositions 1 to 3 was applied to a non-flat SiN wafer by the following procedure, and the gap filling property of each composition was evaluated.

Each composition was applied to a stepped SiN wafer (manufactured by Advanced Materials Technology, Inc.) having a trench with a width of about 10 nm and a height of 500 nm and having a top part with a width of 10 nm using a spin coater (MS-150A, manufactured by Mikasa Co., Ltd.) at 1,500 rpm. The wafer was subjected to multi-step bake in which the wafer was baked on a hot plate in an air atmosphere at 250° C. for 90 seconds and then at 450° C. for 90 seconds. The wafer was further baked in a nitrogen atmosphere at 450° C. for 1 hour to produce a coating from the composition. A section of the wafer with the coating was prepared, and its trench region was observed in a photograph taken by a SEM (S-5500, manufactured by Hitachi High-Tech Fielding Corporation). The filling property of the composition was evaluated as follows. The evaluation results are shown in Table 2.

A: The composition successfully filled gaps so that no gap with voids or pores was found.

B: The composition failed to sufficiently fill gaps so that a gap with voids or pores was present.

Examples 3-1 to 3-11 and Comparative Examples 3-1 to 3-3: Evaluation of Heat Resistance Each of compositions 1 to 11 and comparative compositions 1 to 3 was applied to a Si wafer by the following procedure, and the heat resistance of each composition was evaluated.

Measurement of Thickness Decrease 1

Each composition was applied to a Si bare wafer (manufactured by KST World Corp.) using CLEAN TRACK ACT 12 (manufactured by Tokyo Electron Limited) at 1,500 rpm. The wafer was subjected to multi-step bake in which the wafer was baked on a hot plate in an air atmosphere at 250° C. for 90 seconds and then at 450° C. for 90 seconds. A coating was thus formed from the composition. The thickness of the coating on the wafer was measured with an ellipsometer (M-2000D, manufactured by J.A. Woollam Japan Corporation), and this measured thickness is denoted by "A".

The wafer was further baked in a nitrogen atmosphere at 450° C. for 1 hour. The thickness of the coating on the wafer was measured with the ellipsometer, and this measured thickness is denoted by "B".

Thickness decrease 1 caused by the bake at 450° C. for 1 hour was calculated as $100-B/A\times100$. The results are shown in Table 3.

Measurement of Thickness Decrease 2

Each composition was applied to a Si bare wafer (manufactured by KST World Corp.) using CLEAN TRACK ACT 12 (manufactured by Tokyo Electron Limited) at 1,500 rpm. The wafer was baked on a hot plate in an air atmosphere at 250° C. for 90 seconds to form a coating from the composition. The thickness of the coating on the wafer was measured with an ellipsometer, and this measured thickness is denoted by "C".

The wafer was further baked in a nitrogen atmosphere at 600° C. for 120 seconds. The thickness of the coating on the wafer was measured with the ellipsometer, and this measured thickness is denoted by "D".

Thickness decrease 2 caused by the bake at 600° C. for 120 seconds was calculated as $100-D/C\times100$. The results are shown in Table 3.

The coatings obtained from the compounds according to the present invention showed only a small decrease in thickness when heated, and this confirmed that the coatings had high heat resistance. In the case of the coating obtained from comparative polymer 2, addition of a crosslinking agent and a thermal acid generator didn't exhibit significant effect on prevention of thickness decrease caused by high-temperature bake (600° C.), while in the case of the coatings formed from compounds according to the present invention, addition of a crosslinking agent and a thermal acid generator exhibited a significant effect on prevention of thickness decrease caused by high-temperature bake.

TABLE 2

| | Composition | Compound (parts by mass) | Crosslinking agent (parts by mass) | Thermal acid generator (parts by mass) | Filling property |
|---|---|---|---|---|---|
| Example 2-1 | Composition 1 | G1 (6.0) | — | — | A |
| Example 2-2 | Composition 2 | G1 (3.1) | Crosslinking agent 1 (2.6) | Thermal acid generator 1 (0.062) | A |
| Example 2-3 | Composition 3 | G1 (3.1) | Crosslinking agent 2 (2.6) | Thermal acid generator 1 (0.062) | A |
| Example 2-4 | Composition 4 | G1 (3.1) | Crosslinking agent 3 (2.6) | Thermal acid generator 1 (0.062) | A |
| Example 2-5 | Composition 5 | G2 (6.0) | — | — | A |
| Example 2-6 | Composition 6 | G3 (6.0) | — | — | A |
| Example 2-7 | Composition 7 | G4 (6.0) | — | — | A |
| Example 2-8 | Composition 8 | G5 (6.0) | — | — | A |
| Example 2-9 | Composition 9 | G6 (6.0) | — | — | A |
| Example 2-10 | Composition 10 | G7 (6.0) | — | — | A |
| Example 2-11 | Composition 11 | G8 (6.0) | — | — | A |
| Comparative Example 2-1 | Comparative composition 1 | Comparative polymer 2 (6.0) | — | — | B |
| Comparative Example 2-2 | Comparative composition 2 | Comparative polymer 2 (3.1) | Crosslinking agent 1 (2.6) | Thermal acid generator 1 (0.062) | A |
| Comparative Example 2-3 | Comparative composition 3 | Comparative compound 3 (6.0) | — | — | A |

TABLE 3

| | Composition | A (nm) | B (nm) | Thickness decrease 1 (%) | C (nm) | D (nm) | Thickness decrease 2 (%) |
|---|---|---|---|---|---|---|---|
| Example 3-1 | Composition 1 | 188 | 183 | 2.7 | 204 | 176 | 13.7 |
| Example 3-2 | Composition 2 | 188 | 184 | 2.1 | 207 | 193 | 6.8 |
| Example 3-3 | Composition 3 | 189 | 183 | 3.2 | 206 | 188 | 8.7 |
| Example 3-4 | Composition 4 | 185 | 180 | 2.7 | 202 | 183 | 9.4 |
| Example 3-5 | Composition 5 | 185 | 180 | 2.2 | 209 | 183 | 12.4 |
| Example 3-6 | Composition 6 | 186 | 179 | 3.8 | 202 | 172 | 14.9 |
| Example 3-7 | Composition 7 | 185 | 180 | 2.7 | 205 | 177 | 13.7 |
| Example 3-8 | Composition 8 | 181 | 174 | 3.9 | 202 | 171 | 15.3 |
| Example 3-9 | Composition 9 | 180 | 175 | 2.8 | 203 | 175 | 13.4 |
| Example 3-10 | Composition 10 | 183 | 179 | 2.2 | 204 | 183 | 10.3 |
| Example 3-11 | Composition 11 | 185 | 177 | 4.3 | 202 | 169 | 16.3 |
| Comparative Example 3-1 | Comparative composition 1 | 183 | 170 | 7.1 | 203 | 99 | 51.2 |
| Comparative Example 3-2 | Comparative composition 2 | 182 | 171 | 6 | 200 | 120 | 40 |
| Comparative Example 3-3 | Comparative composition 3 | 180 | 166 | 7.8 | 201 | 98 | 51.2 |

The invention claimed is:

1. A method for manufacturing a semiconductor comprising:

forming an underlayer which comprises applying a layer of an underlayer forming composition to a substrate; and curing the layer to form a coating which is the underlayer and wherein the composition comprises a solvent and a semiconductor material wherein said semiconductor material comprises a compound represented by formula (1):

X—Y wherein

X is a group represented by formula (2):

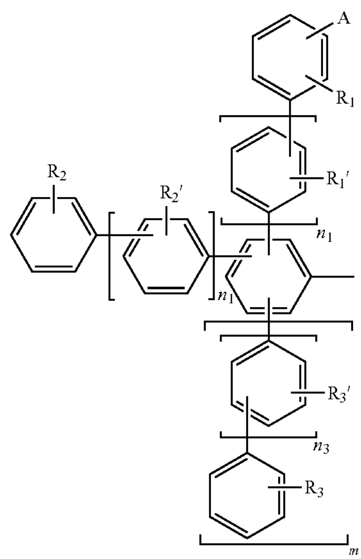

wherein

A is —OH, —$NH_2$, or —SH, $R_1$ is hydrogen, —OH, —$NH_2$, —SH, linear $C_{1-10}$ alkyl, branched $C_{3-10}$ alkyl, or a direct bond to a phenyl ring, $R_{1'}$ is hydrogen, —OH, —$NH_2$, —SH, linear $C_{1-10}$ alkyl, branched $C_{3-10}$ alkyl, or a direct bond to a phenyl ring, $R_2$ is hydrogen, —OH, —$NH_2$, —SH, linear $C_{1-10}$ alkyl, branched $C_{3-10}$ alkyl, or a direct bond to a phenyl ring, $R_{2'}$ is hydrogen, —OH, —$NH_2$, —SH, linear $C_{1-10}$ alkyl, branched $C_{3-10}$ alkyl, or a direct bond to a phenyl ring, $R_3$ is hydrogen, —OH, —$NH_2$, —SH, linear $C_{1-10}$ alkyl, branched $C_{3-11}$) alkyl, or a direct bond to a phenyl ring, $R_{3'}$ is hydrogen, —OH, —$NH_2$, —SH, linear $C_{1-10}$ alkyl, branched $C_{3-10}$ alkyl, or a direct bond to a phenyl ring, $n_1$ is 0, 1, or 2, $n_2$ is 0, 1, or 2, $n_3$ is 0, 1, or 2, m is 0, 1, 2, or 3, and;

Y is represented by formula (3), (4), (5), or (6):

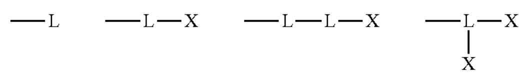

wherein

L is a group represented by formula (7):

(formula 7)

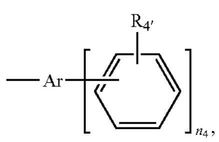

(formula 7), wherein

Ar is unsubstituted or substituted phenyl, $R_{4'}$ is hydrogen, —OH, —$NH_2$, —SH, linear $C_{1-10}$ alkyl, or branched $C_{3-10}$ alkyl, or a direct bond to a phenyl ring, $n_4$ is 0, 1, 2, 3, or 4, forming a layer of a photoresist composition above the underlayer;

curing the photoresist composition to form a photoresist layer;

exposing the substrate coated with the photoresist layer;

developing the exposed substrate to form a resist pattern;

etching with the resist pattern as a mask; and processing the substrate.
2. The method according to claim 1, wherein the compound of formula (1) has 42-120 carbon atoms.
3. The method according to claim 1, wherein the compound of formula (1) is represented by formula (8), (9), (10), or (11):
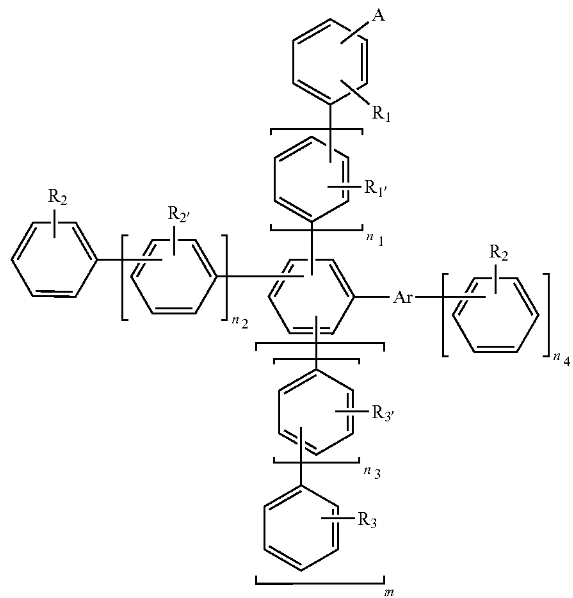
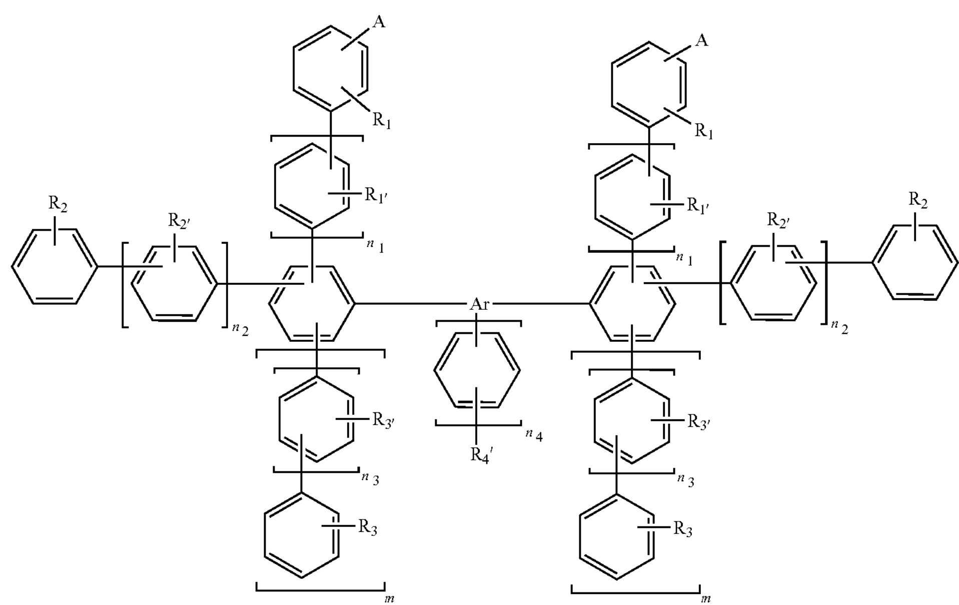

-continued

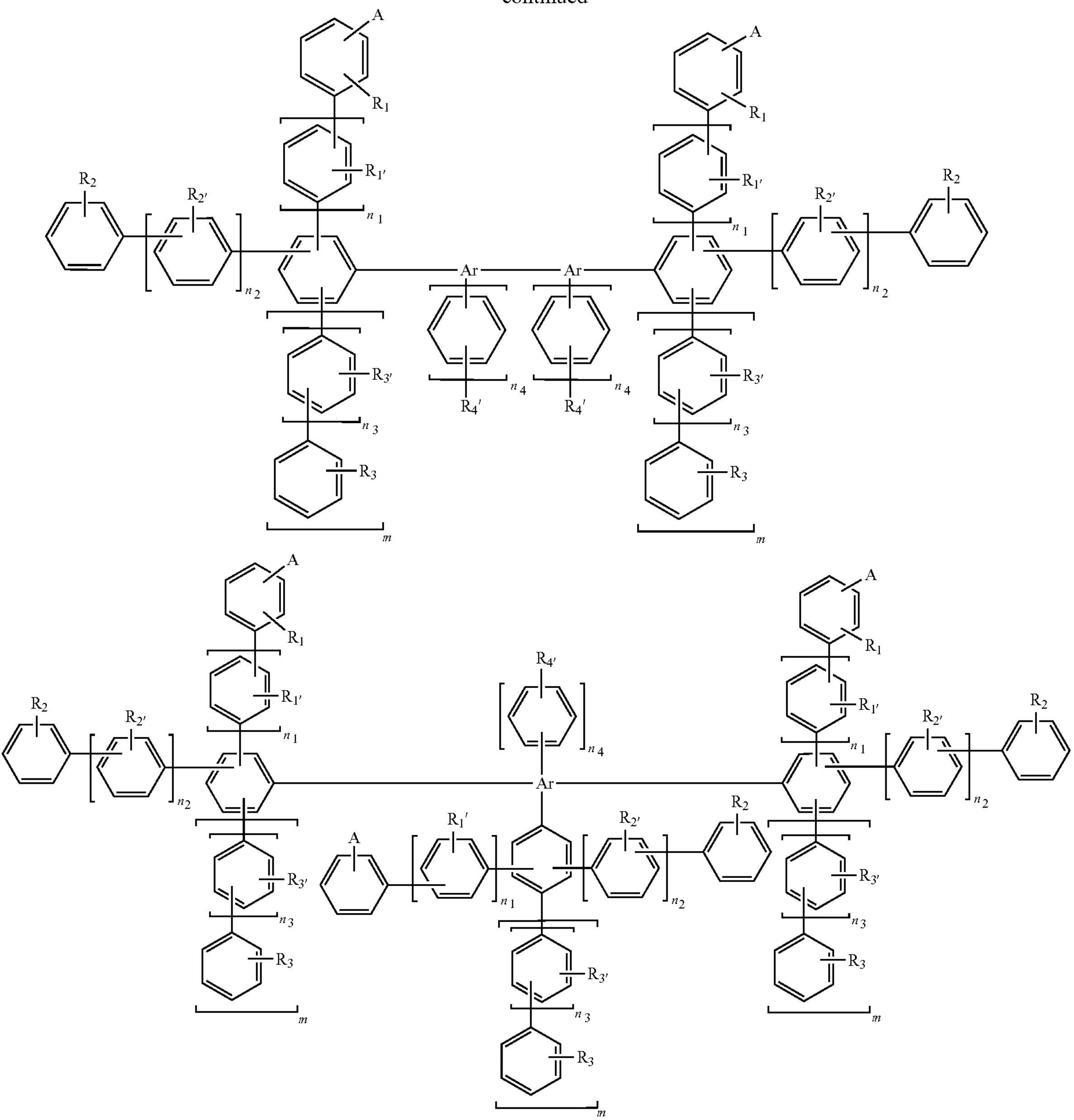

wherein

A, $R_1$, $R_{1'}$, $R_2$, $R_{2'}$, $R_3$, $R_{3'}$, $n_1$, $n_2$, $n_3$, m, Ar, $R_{4'}$, and $n_4$ are each independently as defined in claim 1.

4. The method according to claim 1, wherein the solvent is selected from a group consisting of water; n-pentane; i-pentane; n-hexane; i-hexane; n-heptane; i-heptane; 2,2,4-trimethylpentane; n-octane; i-octane; cyclohexane; methyl cyclohexane; benzene; toluene; xylene; ethylbenzene; trimethylbenzene; methylethylbenzene; n-propylbenzene; i-propylbenzene; diethylbenzene; i-butylbenzene; triethylbenzene; di-i-propylbenzene; n-amylnaphthalene; trimethylbenzene; methanol; ethanol; n-propanol; propanol; n-butanol; i-butanol; sec-butanol; t-butanol; n-pentanol; i-pentanol; 2-methylbutanol; sec-pentanol; t-pentanol; 3-methoxybutanol; n-hexanol; 2-methylpentanol; sec-hexanol; 2-ethylbutanol; sec-heptanol; heptanol-3; n-octanol; 2-ethylhexanol; sec-octanol; n-nonyl alcohol; 2,6-dimethylheptanol-4; n-decanol; sec-undecyl alcohol; trimethylnonyl alcohol; sec-tetradecyl alcohol; sec-heptadecyl alcohol; phenol; cyclohexanol; methylcyclohexanol; 3,3,5-trimethylcyclohexanol; benzyl alcohol; phenylmethylcarbinol; diacetone alcohol; cresol; ethylene glycol; propylene glycol; 1,3-butylene glycol; pentanediol-2,4; 2-methylpentanediol-2,4; hexanediol-2,5; heptanediol-2,4; 2-ethylhexanediol-1,3; diethylene glycol; dipropylene glycol; triethylene glycol; tripropylene glycol; glycerin; acetone; methyl ethyl ketone; methyl n-propyl ketone; methyl n-butyl ketone; diethyl ketone; methyl i-butyl ketone; methyl n-pentyl ketone; ethyl n-butyl ketone; methyl n-hexyl ketone; di-i-butyl ketone; trimethylnonanone; cyclohexanone; cyclopentanone; methylcyclohexanone; 2,4-pentanedione; acetonylacetone; diacetone alcohol; acetophenone; fenchone; ethyl ether; i-propyl ether; n-butyl ether; n-hexyl ether; 2-ethylhexyl ether; ethylene oxide; 1,2-propylene oxide; dioxolane; 4-methyldioxolane; dioxane; dimethyldioxane; ethylene glycol monomethyl ether; ethylene glycol monoethyl ether; ethylene glycol diethyl ether; ethylene glycol mono-n-butyl ether; ethylene glycol mono-n-hexyl ether; ethylene glycol monophenyl ether; ethylene glycol mono-2-ethylbutyl ether; ethylene glycol dibutyl ether; diethylene glycol monomethyl ether; diethylene glycol monoethyl ether; diethylene glycol diethyl ether; diethylene glycol mono-n-butyl ether; diethylene glycol di-n-butyl ether; diethylene glycol mono-n-hexyl ether; ethoxy triglycol; tetraethylene glycol di-n-butyl ether; propylene glycol monomethyl ether; propylene glycol monoethyl ether; propylene glycol monopropyl ether; propylene glycol monobutyl ether; dipropylene glycol monomethyl ether; dipropylene glycol monoethyl ether; dipropylene glycol monopropyl ether; dipropylene glycol monobutyl ether; tripropylene glycol monomethyl ether; tetrahydrofuran; 2-methyltetrahydrofuran; diethyl carbonate; methyl acetate; ethyl acetate; y-butyrolactone; y-valerolactone; n-propyl acetate; i-propyl acetate; n-butyl acetate; i-butyl acetate; sec-butyl acetate; n-pentyl acetate; sec-pentyl acetate; 3-methoxybutyl acetate; methylpentyl acetate; 2-ethylbutyl acetate; 2-ethylhexyl acetate; benzyl acetate; cyclohexyl acetate; methylcyclohexyl acetate; n-nonyl acetate; methyl acetoacetate; ethyl acetoacetate; ethylene glycol monomethyl ether acetate; ethylene glycol monoethyl ether acetate; diethylene glycol monomethyl ether acetate; diethylene glycol monoethyl ether acetate; diethylene glycol mono-n-butyl ether acetate; propylene glycol monomethyl ether acetate; propylene glycol monoethyl ether acetate; propylene glycol monopropyl ether acetate; propylene glycol monobutyl ether acetate; dipropylene glycol monomethyl ether acetate; dipropylene glycol monoethyl ether acetate; glycol diacetate; methoxytriglycol acetate; ethyl propionate; n-butyl propionate; i-amyl propionate; diethyl oxalate; di-n-butyl oxalate; methyl lactate; ethyl lactate; y-butyrolactone; n-butyl lactate; n-amyl lactate; diethyl malonate; dimethyl phthalate; diethyl phthalate; propylene glycol 1-monomethyl ether 2-acetate; propylene glycol monoethyl ether acetate; propylene glycol monopropyl ether acetate; N-methylformamide; N,N-dimethylformamide; N,N-diethylformamide; acetamide; N-methylacetamide; N,N-dimethylacetamide; N-methylpropionamide; N-methylpyrrolidone; dimethyl sulfide; diethyl sulfide; thiophene; tetrahydrothiophene; dimethyl sulfoxide; sulfolane; 1,3-propanesultone; and any mixture of any of these.

5. The method according to claim 1, wherein the amount of the semiconductor material comprising the compound of formula (1) is 2-40 mass % relative to the total amount of the composition.

6. The method according to claim 1, further comprising a surfactant, a crosslinking agent, an acid generator, a radical generator, an agent for enhancing adhesion to substrates, or any combination of any of these.

7. The method according to claim 6, further comprising a surfactant, a crosslinking agent, or an acid generator.

8. The method according to claim 1, wherein the substrate is a non-flat substrate, the height difference between the top part and the lower part of the substrate surface is 10-10,000 nm.

9. The method according to claim 1, wherein conditions for the curing of the underlayer comprise baking at 150-650° C. for 30-180 seconds.

10. The method for manufacturing a semiconductor according to claim 1, further comprising forming wiring in the processed substrate.

11. A semiconductor material comprises a compound represented by formula (1):

X—Y wherein

X is a group represented by formula (2):

(formula 2)

A R$_1$ R$_{1'}$ R$_2$ R$_{2'}$ $n_1$ $n_2$ R$_{3'}$, $n_3$ R$_3$ $m$ wherein

A is —OH, —$NH_2$, or —SH, $R_1$ is hydrogen, —OH, —$NH_2$, —SH, linear $C_{1-10}$ alkyl, branched $C_{3-10}$ alkyl, or a direct bond to a phenyl ring, $R_{1'}$ is hydrogen, —OH, —$NH_2$, —SH, linear $C_{1-10}$ alkyl, branched $C_{3-10}$ alkyl, or a direct bond to a phenyl ring, $R_2$ is hydrogen, —OH, —$NH_2$, —SH, linear $C_{1-10}$ alkyl, branched $C_{3-10}$ alkyl, or a direct bond to a phenyl ring, $R_{2'}$ is hydrogen, —OH, —$NH_2$, —SH, linear $C_{1-10}$ alkyl, branched $C_{3-10}$ alkyl, or a direct bond to a phenyl ring, $R_3$ is hydrogen, —OH, —$NH_2$, —SH, linear $C_{1-10}$ alkyl, branched $C_{3-10}$ alkyl, or a direct bond to a phenyl ring, $R_{3'}$ is hydrogen, —OH, —$NH_2$, —SH, linear $C_{1-10}$ alkyl, branched $C_{3-10}$ alkyl, or a direct bond to a phenyl ring, $n_1$ is 0, 1, or 2, $n_2$ is 0, 1, or 2, $n_3$ is 0, 1, or 2, m is 0, 1, 2, or 3, and;

Y is represented by formula (3), (4), (5), or (6):

—L

—L—X

—L—L—X

—L—X
 |
 X wherein

L is a group represented by formula (7):

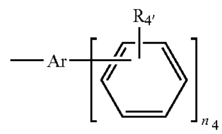

wherein

Ar is unsubstituted or substituted phenyl, $R_{4'}$ is hydrogen, —OH, —$NH_2$, —SH, linear $C_{1-10}$ alkyl, or branched $C_{3-10}$ alkyl, or a direct bond to a phenyl ring, $n_4$ is 0, 1, 2, 3, or 4.

12. A composition comprising a semiconductor material according to claim 11 and a solvent.

13. An underlayer-forming composition consisting of the composition according to claim 12.

14. A compound represented by formula (9)':

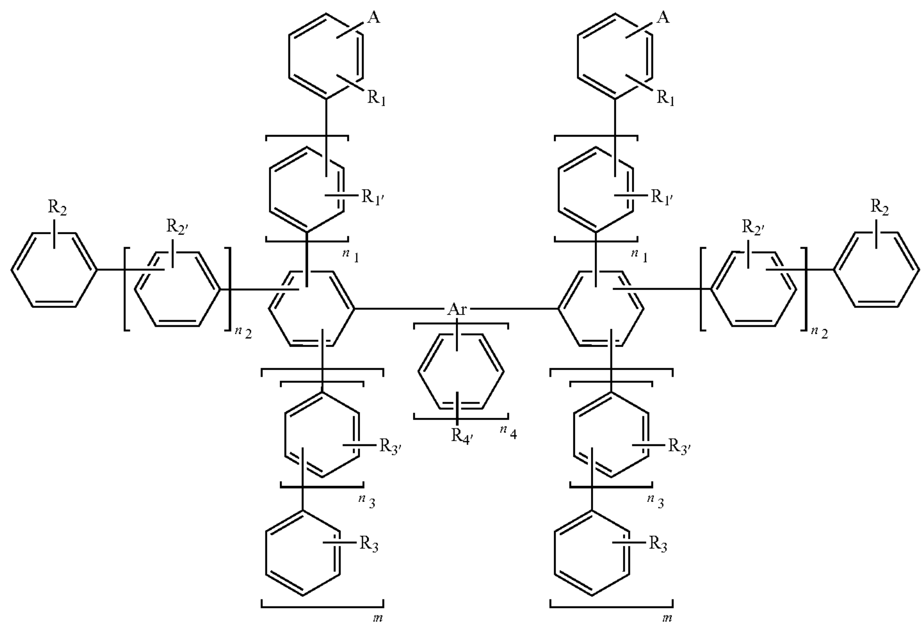

wherein

A is —OH, —$NH_2$, or —SH, $R_1$ is hydrogen, —OH, —$NH_2$, —SH, linear $C_{1-10}$ alkyl, branched $C_{3-10}$ alkyl, or a direct bond to a phenyl ring, $R_{1'}$ is hydrogen, —OH, —$NH_2$, —SH, linear $C_{1-10}$ alkyl, branched $C_{3-10}$ alkyl, or a direct bond to a phenyl ring, $R_2$ is hydrogen, —OH, —$NH_2$, —SH, linear $C_{1-10}$ alkyl, branched $C_{3-10}$ alkyl, or a direct bond to a phenyl ring, $R_{2'}$ is hydrogen, —OH, —$NH_2$, —SH, linear $C_{1-10}$ alkyl, branched $C_{3-10}$ alkyl, or a direct bond to a phenyl ring, $R_3$ is hydrogen, —OH, —$NH_2$, —SH, linear $C_{1-10}$ alkyl, branched $C_{3-10}$ alkyl, or a direct bond to a phenyl ring, $R_{3'}$ is hydrogen, —OH, —$NH_2$, —SH, linear $C_{1-10}$ alkyl, branched $C_{3-10}$ alkyl, or a direct bond to a phenyl ring, $n_1$ is 0, 1, or 2, $n_2$ is 0, 1, or 2, $n_3$ is 0, 1, or 2, m is 0, 1, 2, or 3, and;

Ar is a $C_{6-20}$ aromatic hydrocarbon ring unsubstituted or substituted by a substituent selected from —OH, —$NH_2$, —SH, linear $C_{1-10}$ alkyl, or branched $C_{3-10}$ alkyl,
$R_{4'}$ is hydrogen, —OH, —$NH_2$, —SH, linear $C_{1-10}$ alkyl, branched $C_{3-10}$ alkyl, or a direct bond to a phenyl ring, and
$n_4$ is 0, 1, 2, 3, or 4,
provided that the following compounds are excluded:
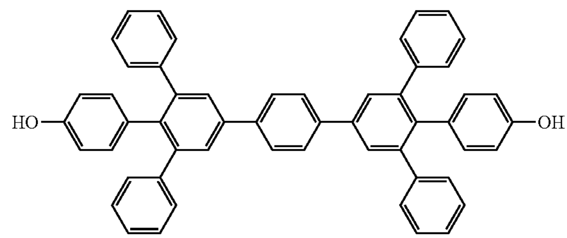
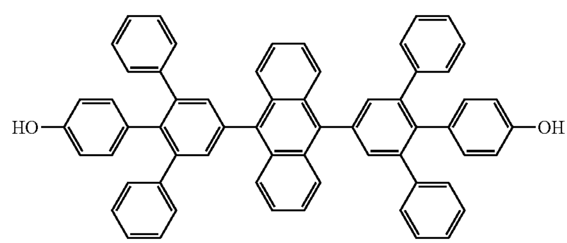
-continued
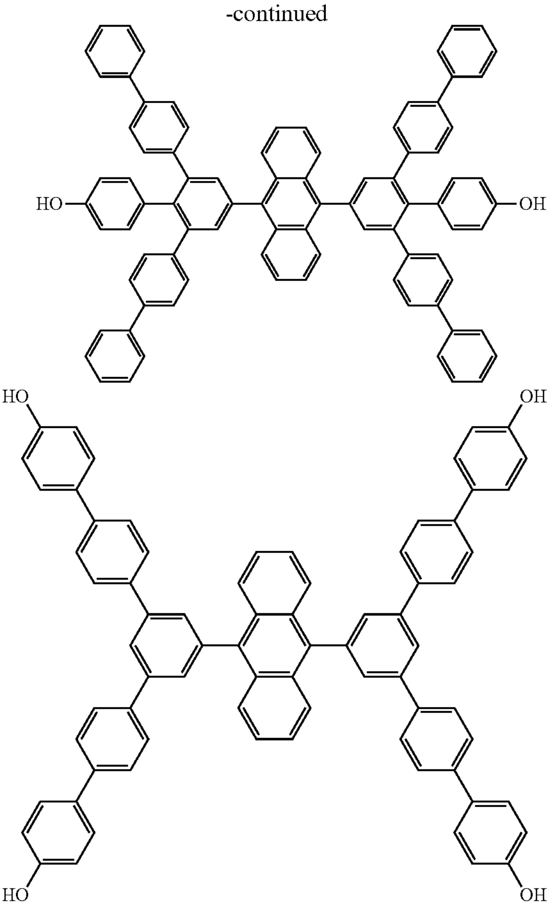
* * * * *